(12) United States Patent
Wheatley et al.

(10) Patent No.: US 12,416,526 B2
(45) Date of Patent: Sep. 16, 2025

(54) OPTICAL STACK, OPTICAL DEVICE AND OPTICAL CONSTRUCTION

(71) Applicant: Solventum Intellectual Properties Company, Maplewood, MN (US)

(72) Inventors: John A. Wheatley, Stillwater, MN (US); Dawn V. Muyres, Stillwater, MN (US); Jason W. Bjork, Cottage Grove, MN (US); Mark August Roehrig, Stillwater, MN (US); Gilles J. Benoit, Minneapolis, MN (US); Theresa J. Gerten, Inver Grove Heights, MN (US); Zhaohui Yang, North Oaks, MN (US); Audrey A. Sherman, Woodbury, MN (US); Bharat R. Acharya, Woodbury, MN (US); Edward J. Kivel, Stillwater, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 96 days.

(21) Appl. No.: 18/279,264

(22) PCT Filed: Feb. 1, 2022

(86) PCT No.: PCT/IB2022/050860
§ 371 (c)(1),
(2) Date: Aug. 29, 2023

(87) PCT Pub. No.: WO2022/185129
PCT Pub. Date: Sep. 9, 2022

(65) Prior Publication Data
US 2024/0151586 A1    May 9, 2024

Related U.S. Application Data

(60) Provisional application No. 63/200,322, filed on Mar. 1, 2021.

(51) Int. Cl.
*G01J 3/51* (2006.01)
*G01J 3/02* (2006.01)
(Continued)

(52) U.S. Cl.
CPC ............. *G01J 3/513* (2013.01); *G01J 3/0264* (2013.01); *G01J 3/0267* (2013.01);
(Continued)

(58) Field of Classification Search
CPC ........ G01J 3/513; G01J 3/0264; G01J 3/0267; G01J 3/0275; G01J 3/10; G01J 3/4406;
(Continued)

(56) References Cited

U.S. PATENT DOCUMENTS

| | | |
|---|---|---|
| 2005/0110999 A1 | 5/2005 | Erdogan et al. |
| 2010/0193704 A1* | 8/2010 | Pratt .................. G01N 21/6428 250/459.1 |

(Continued)

FOREIGN PATENT DOCUMENTS

JP    2020008667 A    1/2020

OTHER PUBLICATIONS

International Search report for PCT International Application No. PCT/IB2022/050860, mailed on May 6, 2022, 4 pages.

*Primary Examiner* — Tarifur R Chowdhury
*Assistant Examiner* — Kaitlyn E Kidwell

(57) ABSTRACT

An optical device for sensing a presence of an analyte in a person includes a light source, an optical stack, and a reader. The light source emits a first light having a first wavelength. The optical stack is placed on the a skin of the person and includes a sensor material and an optical filter. The sensor material emits a second light having a second wavelength when irradiated with the first light. An optical property of the second light is sensitive to the presence of the analyte. The optical filter is disposed on the sensor material and includes
(Continued)

at least ten microlayers. The optical filter has different first and second transmittances at the respective first and second wavelengths.

14 Claims, 17 Drawing Sheets

(51) Int. Cl.
*G01J 3/10* (2006.01)
*G01J 3/44* (2006.01)
*G01J 3/46* (2006.01)

(52) U.S. Cl.
CPC ............... *G01J 3/0275* (2013.01); *G01J 3/10* (2013.01); *G01J 3/4406* (2013.01); *G01J 2003/468* (2013.01); *G01J 2003/516* (2013.01)

(58) Field of Classification Search
CPC .......... G01J 2003/468; G01J 2003/516; A61B 5/0075; A61B 5/14552; A61B 5/14539; A61B 5/14546; A61B 5/6833; A61B 2562/0233; A61B 2562/12; G01N 21/27; G01N 21/255; G01N 21/474; G01N 2021/6471
See application file for complete search history.

(56) References Cited

U.S. PATENT DOCUMENTS

| | | |
|---|---|---|
| 2014/0151575 A1 | 6/2014 | Hillmer et al. |
| 2017/0191870 A1 | 7/2017 | Ockenfuss |
| 2018/0156731 A1 | 6/2018 | Won et al. |
| 2021/0156803 A1* | 5/2021 | Ueno ................. G01N 21/6458 |

\* cited by examiner

OPTICAL STACK, OPTICAL DEVICE AND OPTICAL CONSTRUCTION

CROSS REFERENCE TO RELATED APPLICATIONS

This application is a national stage filing under 35 U.S.C. 371 of PCT/IB2022/050860, filed Feb. 1, 2022, which claims the benefit of Provisional Application No. 63/200,322, filed Mar. 1, 2021, the disclosures of which are incorporated by reference in their entireties herein.

TECHNICAL FIELD

The present disclosure relates generally to an optical stack, and in particular, to an optical stack, an optical device, and an optical construction.

BACKGROUND

Sensing and monitoring certain analytes may be required in various applications. For example, sensing and monitoring oxygen levels may be required in certain situations.

SUMMARY

In a first aspect, the present disclosure provides an optical stack. The optical stack includes a test sample disposed on a first optical filter. The test sample is configured to convert at least a portion of an incident excitation light having an excitation wavelength to a converted light having a converted wavelength different from the excitation wavelength. The first optical filter includes a plurality of microlayers numbering at least 20 in total. Each of the microlayers has an average thickness of less than about 500 nanometers (nm). The plurality of microlayers has an optical transmittance $T1 \geq 20\%$ at the excitation wavelength and at a first incident angle. The plurality of microlayers has an optical transmittance $T2 \geq 20\%$ at the converted wavelength and at a second incident angle. The plurality of microlayers has an optical reflectance $R1 \geq 40\%$ at at least one of the excitation and converted wavelengths and at at least one of the first and second incident angles. For the at least one of the excitation and converted wavelengths, the optical transmittance of the first optical filter changes by at least a factor of 2 when the incident angle corresponding to the at least one of the excitation and converted wavelengths changes to the incident angle corresponding to the other one of the excitation and converted wavelengths.

In a second aspect, the present disclosure provides an optical device for sensing a presence of an analyte. The optical device includes a sensor material emitting a second light having a second wavelength when irradiated with a first light having a different first wavelength. A first optical property of the emitted second light is sensitive to the presence of the analyte. The optical device further includes an optical filter disposed on the sensor material. The optical filter includes a plurality of microlayers numbering at least 20 in total. Each of the microlayers has an average thickness of less than about 500 nm. A second optical property of the optical filter has first and second values at the respective first and second wavelengths. The first value is different from the second value by at least a factor of 2.

In a third aspect, the present disclosure provides an optical device for sensing a presence of an analyte. The optical device includes a sensor material emitting a second light having a second wavelength when irradiated with a first light having a different first wavelength. A first optical property of the emitted second light is sensitive to the presence of the analyte. The optical device further includes an optical filter disposed on the sensor material. The optical filter includes a plurality of microlayers numbering at least 20 in total. Each of the microlayers has an average thickness of less than about 500 nm. For at least a second incident angle, an optical transmission of the plurality of microlayers versus wavelength includes a transmission band edge disposed between the first and second wavelengths.

In a fourth aspect, the present disclosure provides an optical construction for sensing a presence of an analyte. The optical construction includes a sensor material disposed between first and second partial mirrors. For a substantially normally incident light and a predetermined wavelength range from about 400 nm to about 1000 nm, each of the first and second partial mirrors transmits at least 50% of the incident light for a first wavelength in the predetermined wavelength range and reflects at least 50% of the incident light for a different second wavelength in the predetermined wavelength range.

In a fifth aspect, the present disclosure provides an optical device for sensing a presence of an analyte. The optical device includes a sensor material emitting a second light having a second wavelength when irradiated with a first light having a different first wavelength. A first optical property of the emitted second light is sensitive to the presence of the analyte. The optical device further includes an optical filter disposed on the sensor material. The optical filter includes a plurality of microlayers numbering at least 10 in total. Each of the microlayers has an average thickness of less than about 750 nm. For a first incident angle, an optical transmittance of the plurality of microlayers versus wavelength includes at least first and second peaks with respective first and second full width at half maxima (FWHM). The first FWHM includes the first wavelength, but not the second wavelength. The second FWHM includes the second wavelength, but not the first wavelength. Each of the first and second FWHMs is less than about 300 nm wide. For a different second incident angle, an optical transmittance of the plurality of microlayers versus wavelength is less than about 10% at the first wavelength, and includes at least a third peak with a corresponding third FWHM. The third FWHM includes the second wavelength, but not the first wavelength.

In a sixth aspect, the present disclosure provides an optical device for sensing a presence of an analyte in a person. The optical device includes a light source configured to emit a first light having a first wavelength. The optical device further includes a patch configured to be placed on a skin of the person. The patch includes a sensor material emitting a second light having a second wavelength when irradiated with the first light. A first optical property of the emitted second light is sensitive to the presence of the analyte. The patch further includes an optical filter disposed on the sensor material. The optical filter includes a plurality of microlayers numbering at least 10 in total. Each of the microlayers has an average thickness of less than about 750 nm. The optical filter includes different first and second transmittances at the respective first and second wavelengths. The optical device further includes a reader configured to read at least one of an intensity of the second light and at least an image of a portion of at least one of the sensor material and the optical filter.

BRIEF DESCRIPTION OF THE DRAWINGS

Exemplary embodiments disclosed herein may be more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labeled with the same number.

DETAILED DESCRIPTION

Figure 1A:
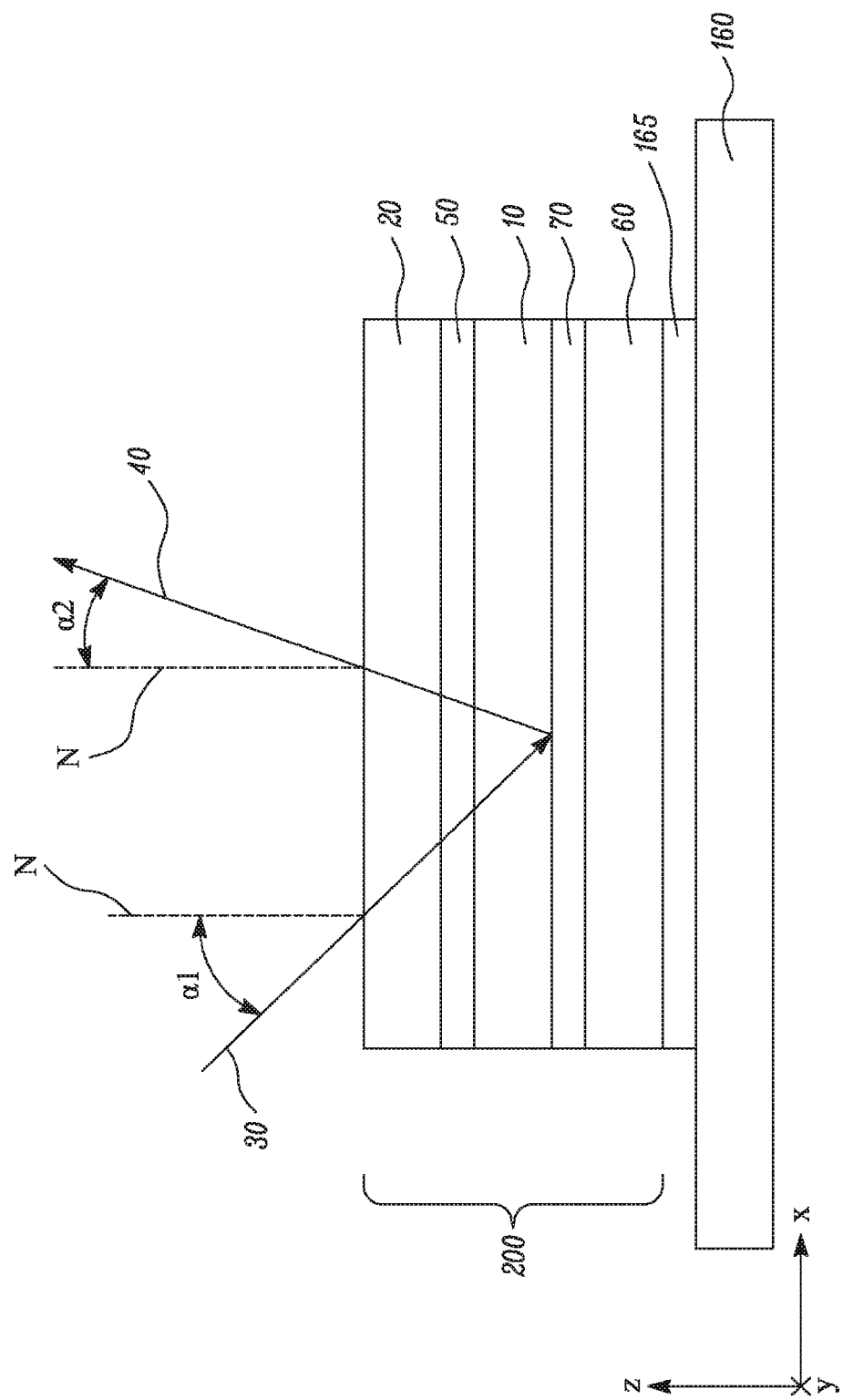
FIG. 1A is a schematic sectional view of an optical stack, according to an embodiment of the present disclosure.

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

The present disclosure relates to an optical stack, an optical device including the optical stack, and an optical construction. The optical stack, the optical device and the optical construction may be used for sensing a presence of an analyte.

Sensing and monitoring an analyte, such as oxygen, may be required in various applications. It may be important to monitor oxygen levels of a person in certain applications, for example, medical applications. Conventional techniques for monitoring oxygen levels include fingertip pulse oximeters, transcutaneous oximetry, etc. However, conventional techniques may rely on blood flow to predict tissue health, and therefore, a compromised perfusion can lead to inaccurate readings.

The present disclosure relates to an optical stack. The optical stack includes a test sample disposed on a first optical filter. The test sample is configured to convert at least a portion of an incident excitation light having an excitation wavelength to a converted light having a converted wavelength different from the excitation wavelength. The first optical filter includes a plurality of microlayers numbering at least 20 in total. Each of the microlayers has an average thickness of less than about 500 nanometers (nm). The plurality of microlayers has an optical transmittance $T1 \geq 20\%$ at the excitation wavelength and at a first incident angle. The plurality of microlayers has an optical transmittance $T2 \geq 20\%$ at the converted wavelength and at a second incident angle. The plurality of microlayers has an optical reflectance $R1 \geq 40\%$ at at least one of the excitation and converted wavelengths and at at least one of the first and second incident angles. For at least one of the excitation and converted wavelengths, the optical transmittance of the first optical filter changes by at least a factor of 2 when the incident angle corresponding to the at least one of the excitation and converted wavelengths changes to the incident angle corresponding to the other one of the excitation and converted wavelengths.

The optical stack of the present disclosure is used in an optical device to sense a presence of an analyte, for example, oxygen. Specifically, the optical stack may be used to sense oxygen in a skin tissue of the person. The test sample of the optical stack may include a photoluminescent material. The photoluminescent material may include a fluorescent material or a phosphorescent material, or a combination of both. The test sample may absorb a portion of the incident excitation light and may then transmit the converted light. In some cases, the converted light has a longer wavelength, and therefore lower energy, than the incident excitation light. The transmitted converted light may have a different color, such as red or green, from that of the excitation color. This phenomenon is generally known as fluorescence.

Oxygen is typically an efficient quencher of fluorescence, i.e., its presence decreases an optical intensity of the fluorescence or the converted light. Therefore, a decrease in the optical intensity of the converted light may be noted by an optical sensor to sense oxygen in the skin tissue. Hence, the optical stack including a fluorescent test sample material may be used in the optical device to sense the presence of oxygen.

Further, the test sample may have to be irradiated with the incident excitation light having the excitation wavelength to cause fluorescence. The first optical filter including the plurality of microlayers may have a relatively high optical transmittance at the excitation wavelength and at the first incident angle corresponding to the incident excitation light, such that at least a portion of the incident excitation light having the excitation wavelength is transmitted by the first optical filter and further absorbed by the test sample. Further, the first optical filter has a relatively high optical transmittance at the converted wavelength and at the second incident angle corresponding to the converted light, such that at least a portion the converted light having the converted wavelength is transmitted by the first optical filter, and a sensor or a viewer may observe a colored light emitted by the test sample. The optical intensity of the converted light may decrease with increase in oxygen level in the vicinity of the test sample.

Hence, the optical stack or a combination of the first optical filter and the test sample may enable the optical device to sense oxygen in various locations, such as skin tissue. The optical stack may also be used to sense the presence of other analytes, for example, by varying the properties of the test sample, as per desired applications. The optical stack of the present disclosure may allow direct sensing of oxygen in the skin tissue without relying on blood flow. Therefore, the optical stack may allow accurate sensing of oxygen. The optical stack may be used as a patch that can be removably applied on a skin of the person to facilitate non-invasive sensing and monitoring of oxygen levels.

Further, a change in the optical intensity of the converted light with an increase in oxygen concentration may allow accurate determination of oxygen level or concentration. Various optical readers or sensors may be used in combination with the optical stack for determining the present of analytes. Further, various other devices, such as controllers, electronic devices (e.g., smartphones), etc., may be combined with the optical stack as per desired application attributes. In some cases, additional layers may be combined with the first optical filter. Such optical layers may include secondary optical filters, light redirecting layers, protective layers, sensing layers, etc.

Moreover, the first optical filter may ensure that the test sample receives at least a portion of the incident excitation light having the excitation wavelength and incident at the first incident angle. The first optical filter may further ensure that at least a portion of the converted light having the converted wavelength and incident at the second incident angle is transmitted for further analysis. Therefore, the first optical filter may provide both spectral filtering (based on wavelength) and spatial filtering (based on incident angle) to allow the test sample to receive the incident excitation light and an optical sensor or reader to receive the converted light from the test sample. Additionally, the first optical filter may be used to substantially block light from other sources (e.g., ambient light) from reaching the test sample. The first optical filter may further substantially prevent light other than the converted light from being transmitted to the optical reader or sensor. For example, in some cases, an optical transmittance of the first optical filter may change by at least a factor of 2 when a wavelength of an incident light changes from the excitation wavelength to the converted wavelength for the first incident angle corresponding to the incident excitation light. Similarly, an optical transmittance of the first optical filter may change by at least a factor of 2 when a wavelength of an incident light changes from the converted wavelength to the excitation wavelength for the second incident angle corresponding to the converted light. In other words, the first optical filter may substantially block or reflect an incident light having the converted wavelength and incident at the first incident angle. Similarly, the first optical filter may substantially block or reflect an incident light having the excitation wavelength and incident at the second incident angle. Therefore, the first optical filter may be optimized for a specific combination of the excitation and converted wavelengths, and the first and second incident angles, and filter out other combinations of wavelengths and incident angles to allow accurate sensing of the analyte. A design of the first optical filter may be conveniently varied as per various application parameters, for example, the excitation wavelength and the first incident angle corresponding to the incident excitation light, the converted wavelength and the second incident angle corresponding to the converted light, a desired thickness of the optical stack, a desired permeability of the analyte, etc.

In some cases, a patch including the first optical filter may be partially permeable to oxygen to allow ambient oxygen to reach the skin tissue in order to promote healing. However, a bottom portion of the patch configured to face the skin may have a greater oxygen permeability than a top portion of the patch configured to face away from the skin. This may allow the test sample to receive a greater amount of oxygen from the skin tissue as compared to ambient oxygen. Thus, an accuracy of oxygen sensing may not be impacted.

Referring now to figures, FIG. 1A illustrates an optical stack 200 according to an embodiment of the present disclosure.

The optical stack 200 defines mutually orthogonal x, y, and z-axes. The x and y-axes are in-plane axes of the optical stack 200, while the z-axis is a transverse axis disposed along a thickness of the optical stack 200. In other words, the x and y-axes are disposed along a plane of the optical stack 200, while the z-axis is perpendicular to the plane of the optical stack 200.

The optical stack 200 includes a test sample 10 disposed on a first optical filter 20. In some embodiments, the test sample 10 can be interchangeably referred to as a sensor material 10. In some embodiments, the first optical filter 20 can be interchangeably referred to as an optical filter 20. In some embodiments, the optical stack 200 can be interchangeably referred to as a patch 200.

The test sample 10 and the first optical filter 20 are disposed along the z-axis. In some embodiments, the first optical filter 20 is bonded to the test sample 10 via a first bonding layer 50. In some embodiments, the first bonding layer 50 includes an adhesive. In some embodiments, the first bonding layer 50 is porous. In some other embodiments, the first bonding layer 50 may include epoxy, lamination, or any other suitable layer.

In some embodiments, the optical stack 200 further includes a second optical filter 60 disposed on the test sample 10 opposite the first optical filter 20. In some embodiments, the second optical filter 60 has a greater oxygen permeability than the first optical filter 20. In some embodiments, the second optical filter 60 is bonded to the test sample 10 via a second bonding layer 70. In some embodiments, the second bonding layer 70 includes an adhesive. In some embodiments, the second bonding layer 70 is porous. In some other embodiments, the second bonding layer 70 may include epoxy, lamination, or any other suitable layer.

In some embodiments, at least one of the first and second optical filters 20, 60 is perforated to allow a passage of at least one of a gas and a liquid therethrough. In some embodiments, the at least one gas may be oxygen.

In some embodiments, the first optical filter 20, the first bonding layer 50, the test sample 10, the second bonding layer 70, and the second optical filter 60 are substantially co-extensive with each other, or of same in-plane dimensions (i.e., length and width). Specifically, the first optical filter 20, the first bonding layer 50, the test sample 10, the second bonding layer 70, and the second optical filter 60 may be substantially co-extensive with each other in the x-y plane. In the illustrated embodiment of FIG. 1A, the first optical filter 20, the first bonding layer 50, the test sample 10, the second bonding layer 70, and the second optical filter 60 are disposed adjacent to each other along the z-axis of the optical stack 200.

In some embodiments, the optical stack 200 may include additional or intermediate films, layers, or components, such as, light control films, light redirecting layers or substrate layers. The optical stack 200 may, in total, be of any suitable thickness based on desired application attributes.

In some embodiments, the optical stack 200 is configured to be placed on a skin 160 of a person. In some embodiments, the optical stack 200 is bonded to the skin 160 via a third bonding layer 165. In some embodiments, the third bonding layer 165 includes an adhesive. In some embodiments, the adhesive of the third bonding layer 165 may be a pressure sensitive adhesive. In some embodiments, the third bonding layer 165 is porous. In some embodiments, the optical stack 200 may be used in a medical device, and thus can be attached to the skin 160 by the third bonding layer 165.

Figure 1B:
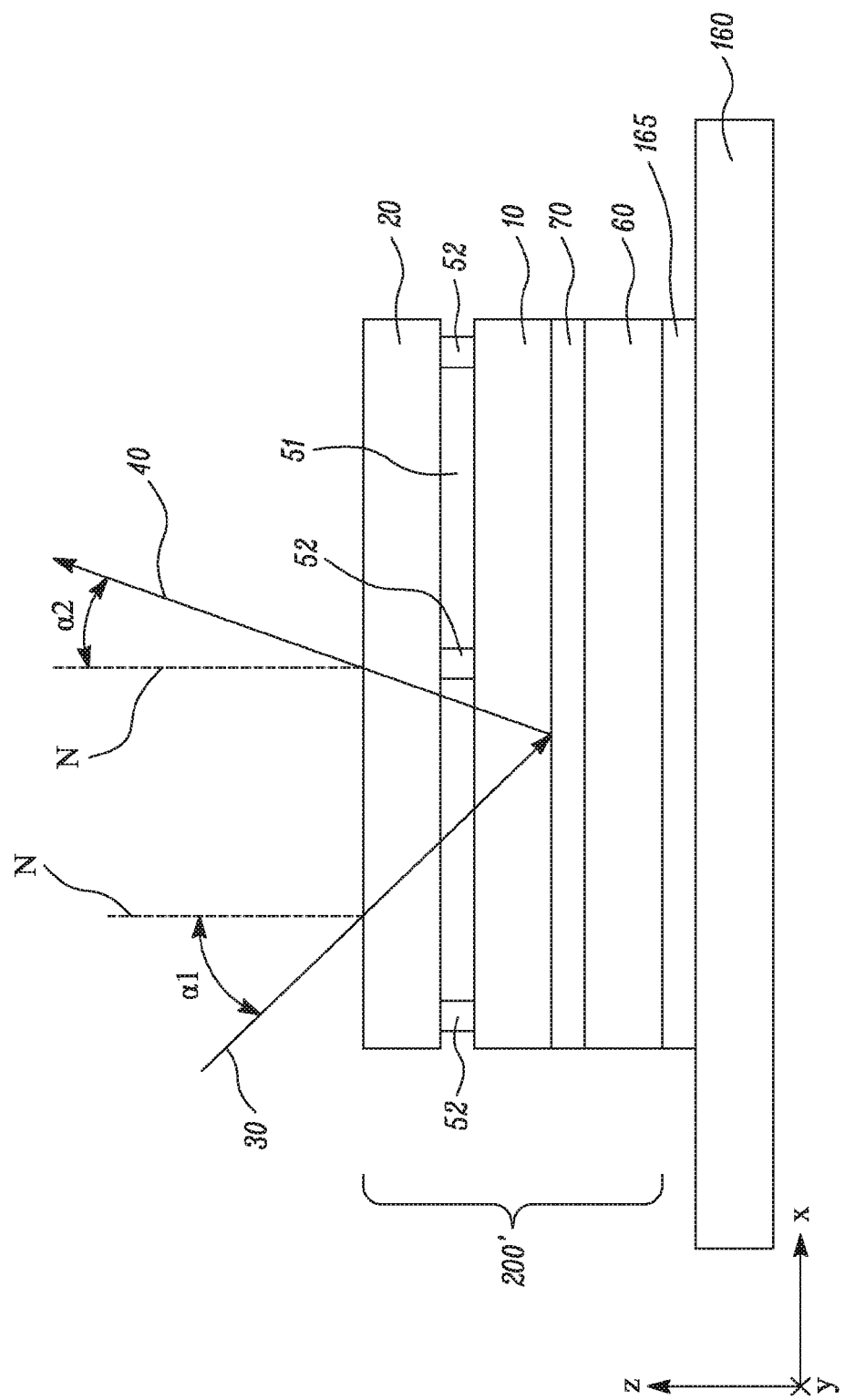
FIG. 1B is a schematic sectional view of an optical stack, according to another embodiment of the present disclosure.

FIG. 1B illustrates an optical stack 200' according to another embodiment of the present disclosure. The optical stack 200' is substantially similar to the optical stack 200. However, in the optical stack 200', the first optical filter 20 and the test sample 10 define an airgap 51 therebetween. In some embodiments, at least one spacer 52 is disposed between the first optical filter 10 and the test sample 10 to maintain the airgap 51. Therefore, in the illustrated embodiment of FIG. 1B, there is no bonding layer between the first optical filter 10 and the test sample 10. Further, in the illustrated embodiment of FIG. 1B, multiple spacers 52 are disposed between the first optical filter 10 and the test sample 10 to maintain the airgap 51. A number of the spacers 52 may be selected based on desired application attributes.

Figure 2:
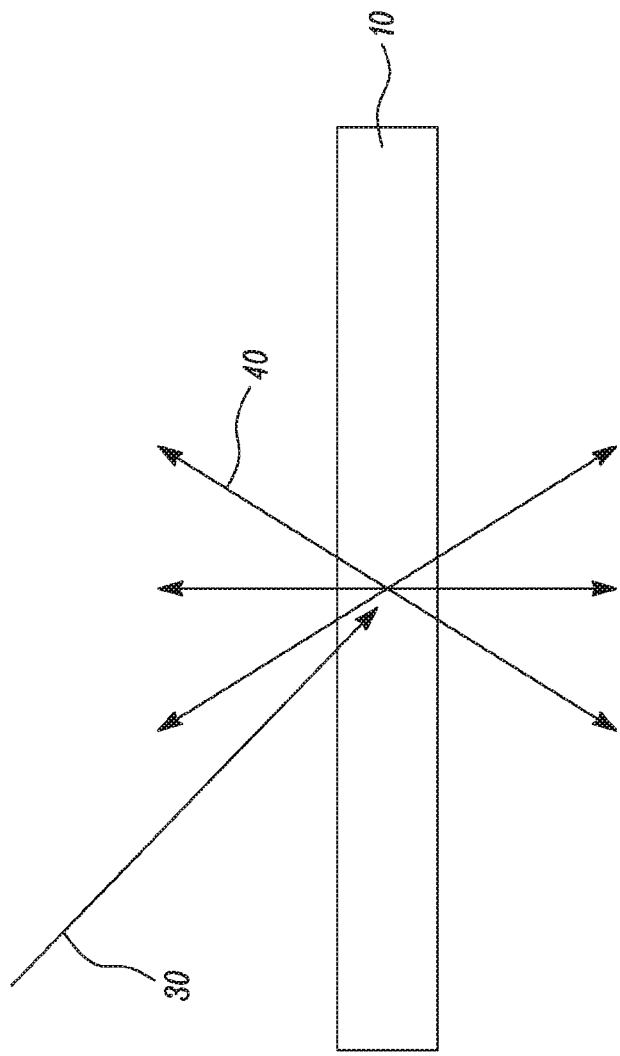
FIG. 2 is a schematic sectional view of a test sample of the optical stack of FIGS. 1A and 1B, according to an embodiment of the present disclosure.

Referring to FIGS. 1A, 1B and 2, the test sample 10 is configured to convert at least a portion of an incident excitation light 30 incident on the first optical filter 20 at a first incident angle α1 to a converted light 40. At least a portion of the converted light 40 exits the optical stack 200 at least after a portion of the converted light 40 is transmitted by the first optical filter at a second incident angle α2. The first and second incident angles α1, α2 are measured with respect to a normal N to the x-y plane of the optical filter 20.

Referring to FIG. 2, the test sample 10 is configured to convert at least the portion of the incident excitation light 30 having an excitation wavelength 31 (shown in FIG. 5A) to the converted light 40 having a converted wavelength 41 (shown in FIG. 5A) different from the excitation wavelength 31.

In some embodiments, the incident excitation light 30 can be interchangeably referred to as a first light 30. In some embodiments, the converted light 40 can be interchangeably referred to as a second light 40. In some embodiments, the excitation wavelength 31 can be interchangeably referred to as a first wavelength 31. In some embodiments, the converted wavelength 41 can be interchangeably referred to as a second wavelength 41. Thus, the sensor material 10 emits the second light 40 having the second wavelength 41 when irradiated with the first light 30 having the different first wavelength 31.

Figure 3:
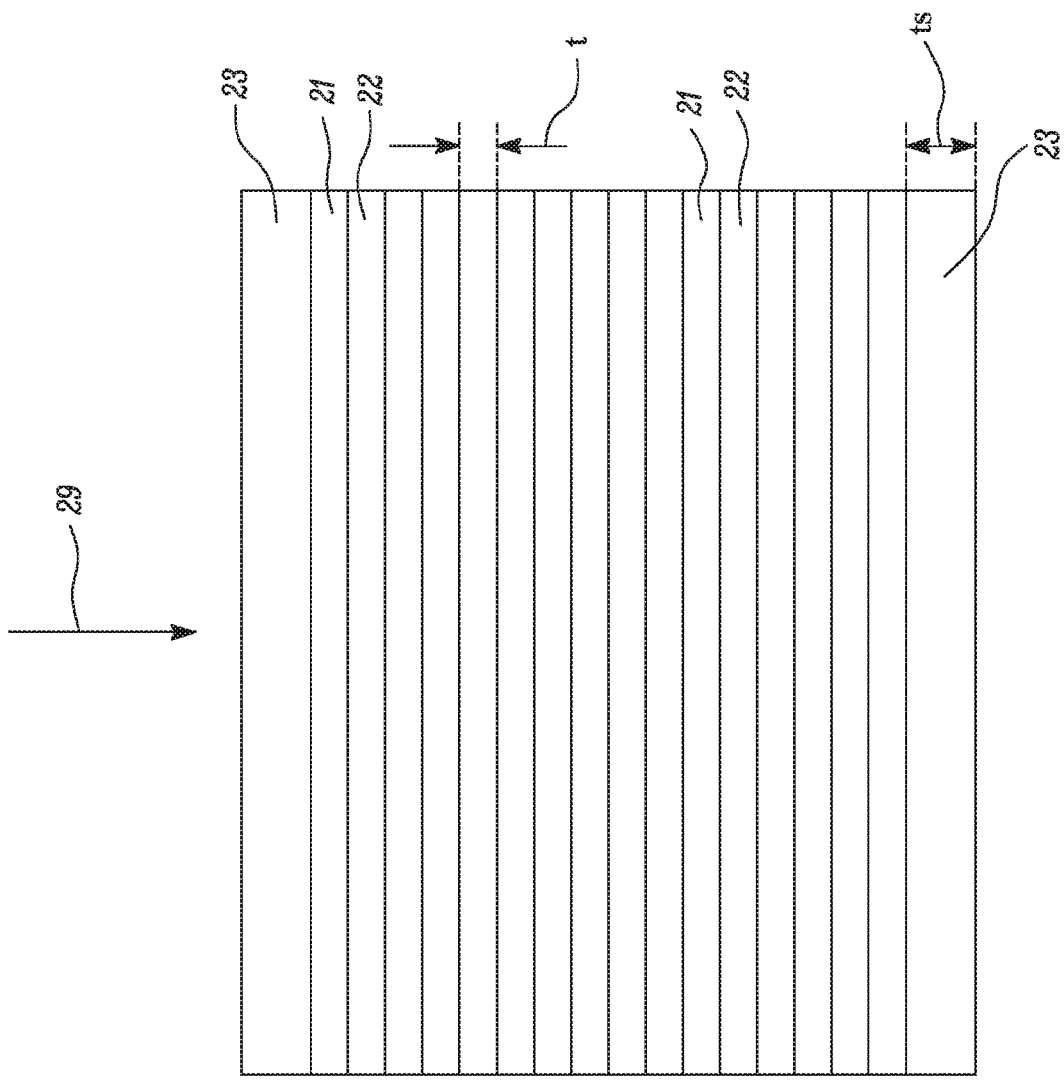
FIG. 3 is a detailed schematic sectional view of a first optical filter of the optical stack of FIGS. 1A and 1B, according to an embodiment of the present disclosure.

Referring to FIG. 3, the first optical filter 20 includes a plurality of microlayers 15 numbering at least 20 in total. In some embodiments, the plurality of microlayers 15 includes a plurality of alternating first and second microlayers 21, 22. The first and second microlayers 21, 22 are arranged along a thickness (i.e., the z-axis) of the first optical filter 20. The plurality of microlayers 15 number at least 10 in total. In some embodiments, the plurality of microlayers 15 number at least 20, at least 50, at least 100, at least 150, at least 200, or at least 250 in total. In some embodiments, desired properties of the first optical filter 20 may be achieved by varying various parameters, such as appropriate material selection of the first and second microlayers 21, 22, thicknesses of the first and second microlayers 21, 22, count of the first and second microlayers 21, 22, etc.

In some embodiments, the microlayers 21, 22 in the plurality of microlayers 15 include one or more of an organic material, an inorganic material, a polymeric layer, and a visible light absorbing material. In some embodiments, the microlayers 21, 22 may include materials including copolymers of polystyrene (PS) and/or poly (methyl methacrylate) (PMMA). In some embodiments, each of the first microlayers 21 includes a high index optical (HIO) layer of polyethylene terephthalate (PET) homopolymer (100 mol % terephthalic acid with 100 mol % ethylene glycol) having a glass transition temperature (Tg) from about 81 degrees Celsius (° C.) to about 83° C. In some embodiments, each of the first microlayers 21 includes a HIO layer of polyethylene naphthalate (PEN). In some embodiments, each of the first microlayers 21 includes a HIO layer of low melt PEN.

In some embodiments, each of the second microlayers 22 includes a low index optical (LIO) layer of copolymer of poly(methyl methacrylate) or coPMMA, available, for example, from Plaskolite, Columbus, OH, under the tradename OPTIX and having a Tg of about 80° C. In some embodiments, each of the second microlayers 22 includes a LIO layer of CoPET (copolymer of polyethylene terephthalate), or CoPEN (copolymer of polyethylene naphthalate), or a blend of polycarbonate and CoPET.

In some embodiments, the first and second microlayers 21, 22 have respective indices of refraction nx1 and nx2 along a same in-plane first direction. In some embodiments, the first direction is along the x-axis. In some embodiments, a magnitude of a difference between nx1 and nx2 is greater than about 0.05. In some embodiments, the magnitude of the difference between nx1 and nx2 may be greater than about 0.10, greater than about 0.15, or greater than about 0.20.

In some embodiments, the first and second microlayers 21, 22 have respective indices of refraction ny1 and ny2 along a same in-plane second direction orthogonal to the first direction. In some embodiments, the second direction is along the y-axis. In some embodiments, a magnitude of a difference between ny1 and ny2 is greater than about 0.05. In some embodiments, the magnitude of the difference between ny1 and ny2 may be greater than about 0.10, greater than about 0.15, or greater than about 0.20.

In some embodiments, the magnitude of the difference between ny1 and ny2 is less than about 0.05. In some embodiments, the magnitude of the difference between ny1 and ny2 may be less than about 0.04, less than about 0.03, less than about 0.02, or less than about 0.01.

In some embodiments, a magnitude of at least one of nx1-ny1 and nx2-ny2 is less than about 0.05. In some embodiments, the magnitude of the at least one of nx1-ny1 and nx2-ny2 may be less than about 0.04, less than about 0.03, less than about 0.02, or less than about 0.01.

Each of the microlayers 21, 22 has an average thickness "t". Specifically, each of the microlayers 15 defines the average thickness "t" along the z-axis. The term "average thickness", as used herein, refers to an average thickness along a plane of a layer. In the illustrated embodiment of FIG. 3, the average thickness "t" is measured along the x-y plane. In some embodiments, each of the microlayers 15 has the average thickness "t" of less than about 500 nanometers (nm). In some embodiments, each of the microlayers 15 has the average thickness "t" of less than about 750 nm. In some embodiments, each of the microlayers 15 has the average thickness "t" of less than about 450 nm, less than about 400 nm, less than about 350 nm, less than about 250 nm, or less than about 200 nm.

In the illustrated embodiment of FIG. 3, the first optical filter 20 further includes at least one skin layer 23. In some embodiments, the at least one skin layer 23 has an average thickness "ts" of greater than about 500 nm. In some embodiments, the at least one skin layer 23 has the average thickness "ts" of greater than about 750 nm, greater than about 1000 nm, greater than about 1500 nm, or greater than about 2000 nm. In the illustrated embodiment of FIG. 3, the first optical filter 20 includes a pair of opposing outermost skin layers 23. The at least one skin layer 23 may act as protective layer of the first optical filter 20. For example, the skin layers 23 of FIG. 3 may act as protective boundary layers (PBL) of the first optical filter 20.

Figure 4:
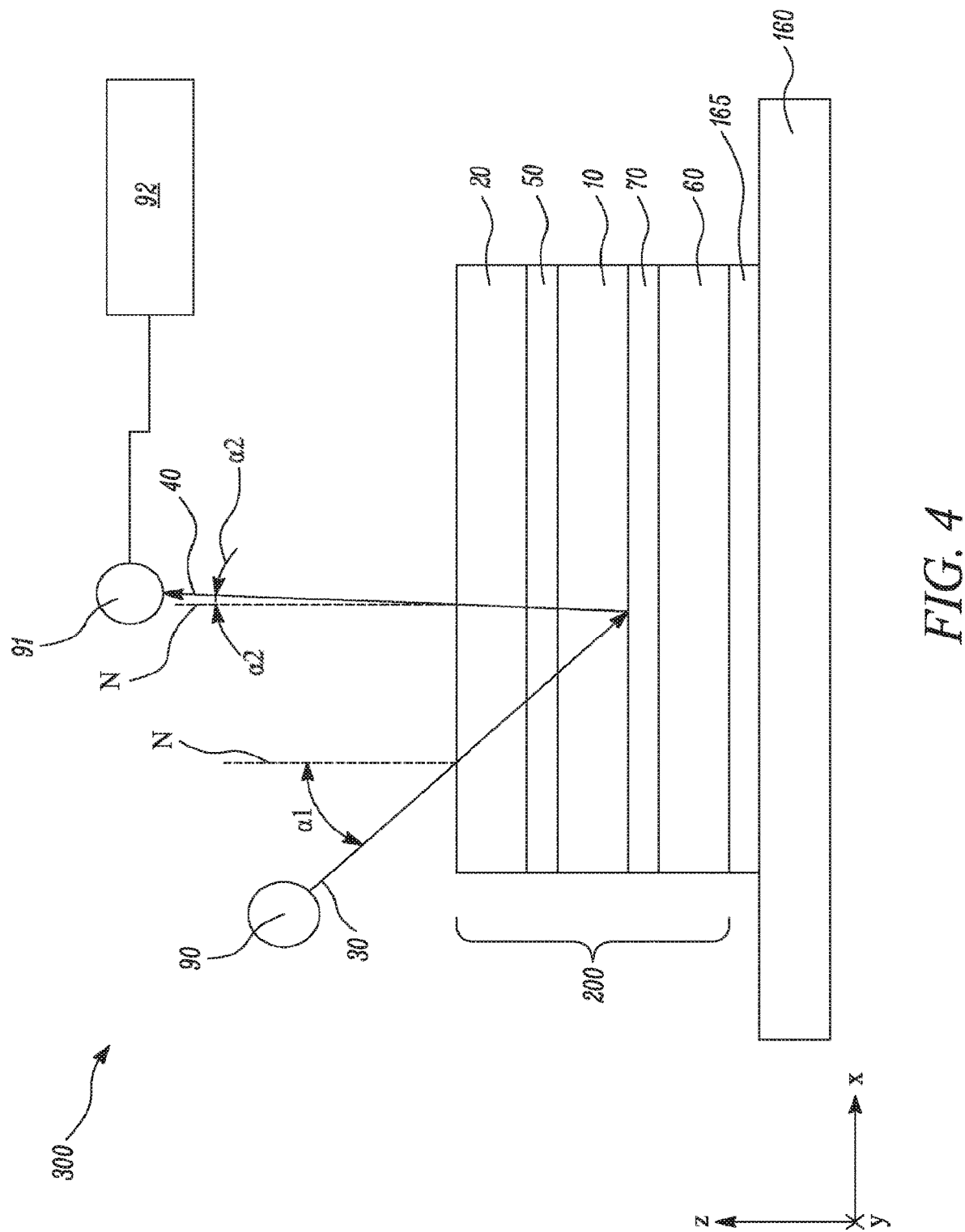
FIG. 4 is a schematic sectional view of an optical device including the optical stack of FIG. 1A, according to an embodiment of the present disclosure.

FIG. 4 illustrates an optical device 300 for sensing a presence of an analyte, according to an embodiment of the present disclosure. In some embodiments, the optical device 300 senses the presence of the analyte in the person. In some embodiments, the optical device 300 is configured to be placed on the skin 160 of the person. The analyte is generally a chemical constituent that is of interest in an analytical or a diagnostic procedure. In some embodiments, the analyte is oxygen. In some embodiments, the analyte includes an analyte that is associated with a biological process. In some examples, the biological process may include metabolism, movements, cell growth and maintenance, responsiveness, respiration, etc. In another example, the biological process may include supplying oxygen by blood to various skin tissues of human body for health and maintenance of cells of skin tissues.

In some embodiments, the analyte is an output of the biological process. For example, while supplying blood to various cells of human body, oxygen is carried by the blood so that each cell may receive sufficient oxygen for its growth. Therefore, in some cases, oxygen is an output of the biological process of blood supply in human body. In some embodiments, the analyte is associated with a characteristic of the biological process. In some embodiments, the characteristic includes one or more of an oxygen level, a pH, and a carbon dioxide level of the biological process.

In some embodiments, the optical device 300 is a medical device. In some embodiments, a medical device includes the optical device 300. In some examples, the medical device may be an instrument, an apparatus, an implement, a machine, a contrivance, an implant, or other similar or related article that is intended for use in diagnosis of a disease or other conditions. In some examples, the medical device may be intended for use in cure, mitigation, treatment, monitoring, or prevention of disease or other conditions. In some examples, the medical device may be intended for use in monitoring physiological status, or physical performance. In some examples, the medical device may be attached or adhered to a desired location, such as a wound or an incision to treat the effects or sequelae of the wound or incision. In some examples, the medical device may be used for sensing the presence of one or more of an analyte, a biological molecule, a liquid, a gas, a cell, a microbe, or a virus. In some examples, the medical device may be used as a part of a medical apparatus or therapy. In some examples, the medical device may be incorporated into an apparatus designed to protect a subject from an environmental factor, such as a welding hood, a helmet, a respirator, sporting gear, firefighting gear, chemical or biological protection gear, radiation or thermal protection gear, or personal armor.

Moreover, in some examples, the medical device may include a wound dressing, a bandage, a skin patch, a medical foam and sponge, a compression wrap, or a medical sensor. In some other examples, the medical device may include garments (e.g., compression hose and socks) worn to treat, monitor, or ameliorate a disease or medical condition. In some examples, the medical device may include a clothing, a watch, a jewelry containing sensors to monitor heart rate and function, blood oxygen level, respiratory rate and function, perspiration production and composition, physiological activity, and the like. In some cases, the medical device may be used to monitor the health status of the person in industrial, emergency, or military settings. In some embodiments, the optical device 300 may be used in the medical device (e.g., wound dressing) for measuring an output, such as an amount of an analyte in or near a wound or incision. In some embodiments, the medical device including the optical device 300 may further include a barrier material capable of controlling the migration of one or more components, such as water, oxygen, bacteria, or viruses, so as to maintain the integrity of the optical device to accurately measure the output in the environment contained within the wound dressing as opposed to the environment outside of the wound dressing.

In some embodiments, the optical device 300 is a wearable device. In some embodiments, a wearable device includes the optical device 300. The wearable device is configured to be worn by the person. In some embodiments, the wearable device is a mask configured to be worn on a face of the person. In some embodiments, the wearable device is a patch configured to be worn on a skin of the person. In some embodiments, the patch includes a wound dressing.

In some embodiments, the optical device 300 is substantially flexible and configured to conform to a curved surface. In some embodiments, the optical device 300 is configured to conform to a curved skin portion of the person. Therefore, the optical device 300 may have an ability to be made in or shaped to a desired curvature.

The optical device 300 includes the optical stack 200, a light source 90, and an optical sensor 91. In some embodiments, the optical sensor 91 can be interchangeably referred to as a reader 91. In some embodiments, the light source 90 is configured to emit the incident excitation light 30 having the excitation wavelength 31 (shown in FIG. 5A). In some embodiments, the light source 90 includes a laser. In some embodiments, the light source 90 includes a vertical-cavity surface-emitting laser (VCSEL). In some embodiments, the light source 90 may include at least one of filament or arc lamps, light emitting diodes (LEDs), linear cold cathode fluorescent tubes, non-linear cold cathode fluorescent tubes, flat fluorescent panels, or external electrode fluorescent lamps.

In some embodiments, the incident excitation light 30 emitted by the light source 90 is generally unpolarized. However, in some cases, the incident excitation light 30 may be at least partially polarized light. For the purpose of explanation, the incident excitation light 30 may be treated as light having an unknown or arbitrary polarization state or distribution of polarization states.

In some embodiments, the test sample 10 includes a photoluminescent material. The photoluminescent material absorbs a photon (mainly UV and blue light), excites one of its electrons to a higher electronic excited state, and then radiates a photon as the electron returns to a lower energy state. In other words, the photoluminescent material emits a light after absorption of photons (electromagnetic radiation). Such a phenomenon is known as photoluminescence. Generally, in photoluminescence, an emitted light has a longer wavelength, and therefore lower energy than an absorbed light.

In some embodiments, the photoluminescent material includes one or more of a fluorescent material and a phosphorescent material. The fluorescent material exhibits fluorescence, and the phosphorescent material exhibits phosphorescence. Fluorescence is relatively a fast process, and some amount of energy is dissipated so that re-emitted light has a lower energy than an absorbed light. In phosphorescence, the phosphorescent material does not immediately re-emit the light it has absorbed. Phosphorescence is emission of light from triplet-excited states, in which the electron in the excited orbital has the same spin orientation as the ground-state electron. Transitions to the ground state are spin-forbidden, and the emission rates are relatively slow. The result is a slow process of radiative transition back to the singlet state, sometimes lasting from milliseconds to seconds to minutes.

The fluorescent material is usually a phosphor that may include solid inorganic materials consisting of a host lattice, usually intentionally doped. Phosphors are usually made from a suitable host material with an added activator. The host materials are typically oxides, nitrides and oxynitrides, sulfides, selenides, halides or silicates of zinc, cadmium, manganese, aluminium, silicon, or various rare-earth metals. The activators prolong the emission time (afterglow).

In some embodiments, the phosphorescent material includes one or more of a porphyrin, a pi-conjugated molecule, and a pi-conjugated polymer. In some embodiments, the test sample 10 includes a gel material.

A first optical property of the emitted second light 40 is sensitive to the presence of the analyte. In some embodiments, the first optical property of the converted light 40 includes an optical intensity of the converted light 40. In some embodiments, the phosphorescent material is oxygen sensitive so that in a presence of oxygen, the optical intensity of the converted light 40 decreases. In some embodiments, the optical intensity of the converted light 40 decreases with increasing partial pressure of oxygen. In other words, oxygen acts as an efficient phosphorescence quencher, as it decreases the optical intensity of the converted light 40 emitted by the phosphorescent material in the test sample 10.

In some embodiments, the photoluminescent material is oxygen sensitive so that in the presence of oxygen, the optical intensity of the converted light 40 decreases. In some embodiments, the optical intensity of the converted light 40 decreases with increasing partial pressure of oxygen. In other words, oxygen acts as a photoluminescence quencher, as it decreases the optical intensity of the converted light 40 emitted by the photoluminescent material in the test sample 10. Therefore, in an absence of oxygen or any other photoluminescence quencher, the optical intensity of the converted light 40 is relatively higher.

Figure 5A:
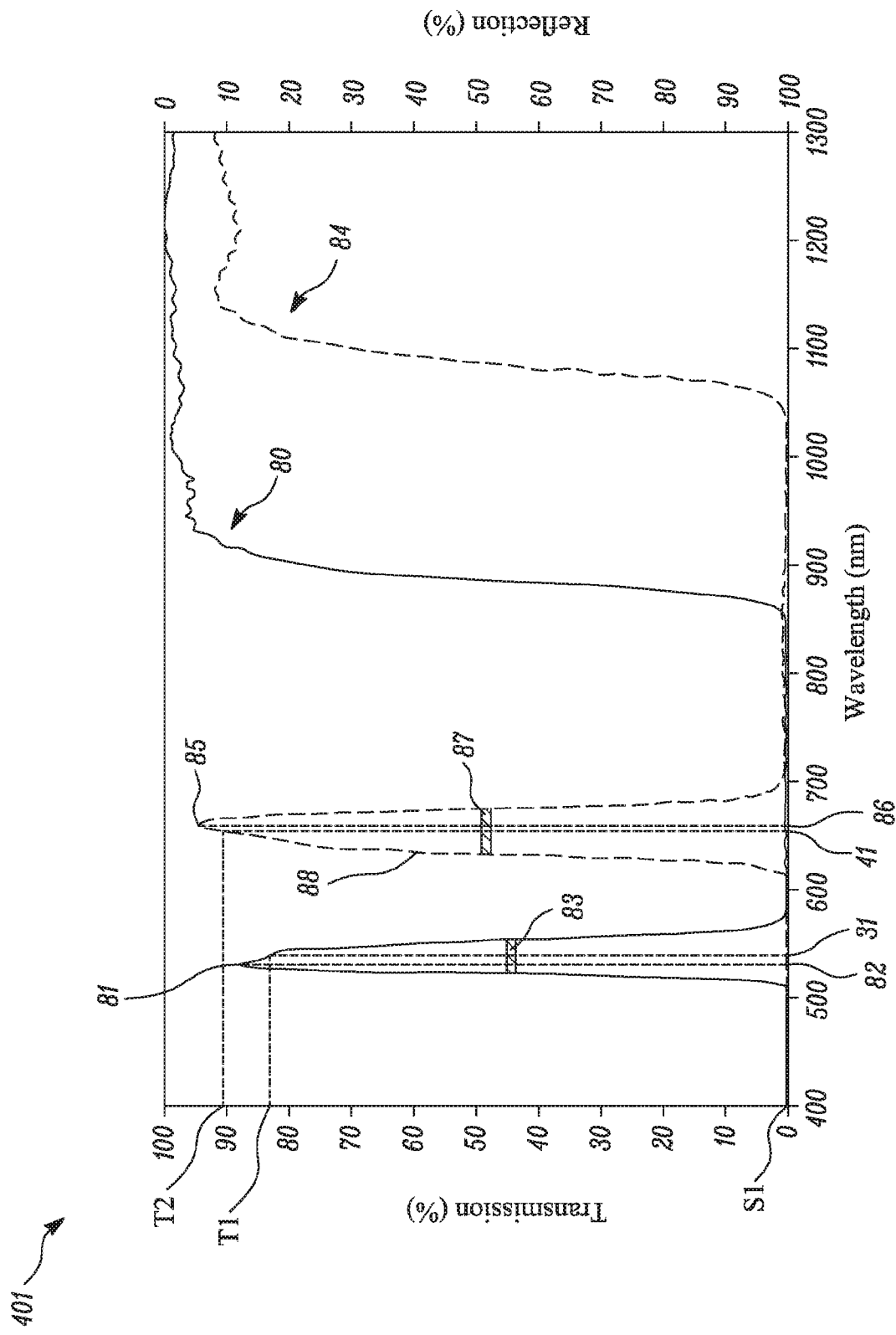
FIG. 5A is a graph illustrating transmission versus wavelength for the first optical filter, according to an embodiment of the present disclosure.

Referring to FIGS. 4 and 5A, the light source 90 configured to emit the first light 30 having the first wavelength 31. In other words, the light source 90 is configured to emit the incident excitation light 30 having the excitation wavelength 31 and incident on the first optical filter 20 at the first incident angle $\alpha 1$. The test sample 10 converts at least a portion of the incident excitation light 30 to the converted light 40 at least after at least a portion of the incident excitation light 30 is transmitted by the first optical filter 20. At least a portion of the converted light 40 exits the optical stack 200 after at least a portion of the converted light 40 is transmitted by the first optical filter 20 at the second incident angle $\alpha 2$.

In some embodiments, the optical sensor 91 is configured to receive and sense the converted light 40 exiting the optical stack 200. In some embodiments, the optical device 300 further includes a controller 92 configured to receive information read by the optical sensor 91.

In some embodiments, the first and second incident angles $\alpha 1$, $\alpha 2$ are within less than about 10 degrees of each other. In some other embodiments, the first and second incident angles $\alpha 1$, $\alpha 2$ are different by at least about 10 degrees. In some embodiments, the first incident angle $\alpha 1$ is greater than about 30 degrees, and the second incident angle $\alpha 2$ is less than about 15 degrees. In some embodiments, the first incident angle $\alpha 1$ is greater than about 35 degrees, greater than about 40 degrees, greater than about 45 degrees, or greater than about 50 degrees. In some embodiments, the second incident angle $\alpha 2$ is less than about 10 degrees, or less than about 5 degrees.

In some embodiments, the excitation wavelength 31 is smaller than the converted wavelength 41. In some embodiments, the excitation and converted wavelengths 31, 41 are both visible wavelengths between about 420 nm to about 680 nm. In some embodiments, one of the excitation and converted wavelengths 31, 41 is a visible wavelength between about 420 nm to about 680 nm, and other one of the excitation and converted wavelengths 31, 41 is an infrared wavelength between about 700 nm to about 2000 nm. In some embodiments, the excitation wavelength 31 is a blue wavelength and the converted wavelength 41 is a green or a red wavelength. In common applications where the test sample 10 is utilized, the excitation wavelength 31 is the blue wavelength or an ultraviolet (UV) wavelength, and the converted wavelength 41 is the green or red wavelength. In some embodiments, the excitation and converted wavelengths 31, 41 are separated by at least 50 nm. In some embodiments, the excitation and converted wavelengths 31, 41 are separated by at least 75 nm, or at least 100 nm. FIG. 5A illustrates an exemplary graph 401 depicting transmission percentage versus wavelength for the plurality of microlayers 15 (shown in FIG. 3) of the first optical filter 20. Wavelength is expressed in nanometers (nm) in the abscissa. Transmission is expressed as transmission percentage in the left ordinate. Reflection is expressed as reflection percentage in the right ordinate. The reflection percentage is complementary to the transmission percentage, i.e., reflection percentage=(100−transmission percentage).

Referring to FIGS. 1A, 1B and 5A, as shown in the graph 401, for the first incident angle $\alpha 1$, an optical transmittance of the plurality of microlayers versus wavelength 80 includes a first peak 81 at a first peak wavelength 82 with a corresponding full width at half maximum (FWHM) 83 that includes the excitation wavelength 31, but not the converted wavelength 41. The optical transmittance of the plurality of microlayers versus wavelength 80 is interchangeably referred to as "the optical transmittance versus wavelength 80". The optical transmittance versus wavelength 80 therefore illustrates a variation of the optical transmittance of the plurality of microlayers 15 of the first optical filter 20 with wavelength for the first incident angle $\alpha 1$. Further, for the second incident angle α2, an optical transmittance of the plurality of microlayers versus wavelength 84 includes a second peak 85 at a second peak wavelength 86 with a corresponding FWHM 87 that includes the converted wavelength 41, but not the excitation wavelength 31. The optical transmittance of the plurality of microlayers versus wavelength 84 is interchangeably referred to as "the optical transmittance versus wavelength 84". The optical transmittance versus wavelength 84 therefore illustrates a variation of the optical transmittance of the plurality of microlayers 15 of the first optical filter 20 with wavelength for the second incident angle α2.

In some embodiments, the first incident angle α1 is an oblique angle of about 55 degrees and the second incident angle α2 is from about 0 degree to 5 degrees. Thus, the first and second incident angles α1, α2 are different by at least about 10 degrees.

In some embodiments, the excitation wavelength 31 is between about 500 nm and about 580 nm, and the converted wavelength 41 is between about 600 nm and about 700 nm.

Referring to the optical transmittance versus wavelength 80 in the graph 401, the plurality of microlayers 15 has an optical transmittance T1 greater than or equal to 20% (i.e., T1≥20%) at the excitation wavelength 31 and at the first incident angle α1. In some embodiments, the plurality of microlayers 15 has the optical transmittance T1≥30%, ≥40%, ≥50%, ≥70%, or ≥80% at the excitation wavelength 31 and at the first incident angle α1. Further, referring to the optical transmittance versus wavelength 84 in the graph 401, the plurality of microlayers 15 has an optical transmittance T2 greater than or equal to 20% (i.e., T2≥20%) at the converted wavelength 41 and at the second incident angle α2. In some embodiments, the plurality of microlayers 15 has the optical transmittance T2≥30%, ≥40%, ≥50%, ≥60%, ≥70%, or ≥80% at the converted wavelength 41 and at the second incident angle α2.

Further, in some embodiments, the second optical filter 60 has an optical transmittance T3 (not shown) greater than or equal to 20% (i.e., T3≥20%) at each of the excitation and converted wavelengths 31, 41 and each of the first and second incident angles α1, α2. In some embodiments, the second optical filter 60 has the optical transmittance T3≥30%, ≥40%, ≥50%, ≥60%, ≥70%, or ≥80% at each of the excitation and converted wavelengths 31, 41 and each of the first and second incident angles α1, α2.

Moreover, the plurality of microlayers 15 has an optical reflectance R1 greater than or equal to 40% (i.e., R1≥40%) at the at least one of the excitation and converted wavelengths 31, 41 and at at least one of the first and second incident angles α1, α2. In some embodiments, the plurality of microlayers 15 has the optical reflectance R1≥50%, ≥60%, ≥70%, ≥80%, or ≥90% at the at least one of the excitation and converted wavelengths 31, 41 and at the at least one of the first and second incident angles α1, a2.

For the at least one of the excitation and converted wavelengths 31, 41, the optical transmittance of the first optical filter 20 changes by at least a factor of 2 when the incident angle corresponding to the at least one of the excitation and converted wavelengths 31, 41 changes to the incident angle corresponding to the other one of the excitation and converted wavelengths 31, 41. In some embodiments, for the at least one of the excitation and converted wavelengths 31, 41, the corresponding optical transmittance of the first optical filter 20 changes by at least a factor of 5, at least a factor of 10, at least a factor of 25, at least a factor of 50, at least a factor of 75, or at least a factor of 100, when the incident angle corresponding to the at least one of the excitation and converted wavelengths 31, 41 changes to the incident angle corresponding to the other one of the excitation and converted wavelengths 31, 41.

For example, for the excitation wavelength 31, the optical transmittance of the first optical filter 20 changes by at least the factor of 2 when the incident angle changes from the first incident angle α1 to the second incident angle α2. Referring to the optical transmittance versus wavelength 80, the first optical filter 20 has the optical transmittance T1 at the excitation wavelength 31 and at the first incident angle α1. Further, the first optical filter 20 has an optical transmittance S2 at the converted wavelength 41 and at the first incident angle α1. In some embodiments, at the first incident angle α1, the first optical filter 20 has the optical transmittance T1≥60% at the excitation wavelength 31, and the optical transmittance S2≤30% at the converted wavelength 41.

Similarly, for the converted wavelength 41, the optical transmittance of the first optical filter 20 changes by at least the factor of 2 when the incident angle changes from the second incident angle α2 to the first incident angle α1. Referring to the optical transmittance versus wavelength 84, the first optical filter 20 has the optical transmittance T2 at the converted wavelength 41 and at the second incident angle α2. Further, the first optical filter 20 has an optical transmittance S1 at the excitation wavelength 31 and at the second incident angle α2. In some embodiments, at the second incident angle α2, the first optical filter 20 has the optical transmittance S1≤30% at the excitation wavelength 31, and the optical transmittance T2≥60% at the converted wavelength 41.

In the illustrated embodiment of FIG. 5A, for a light incident at the first incident angle α1, the first optical filter 20 is substantially transmissive (e.g., optical transmittance≥60%) at the excitation wavelength 31 and is substantially reflective (e.g., optical reflectance≥70%) at the converted wavelength 41. Similarly, for a light incident at the second incident angle α2, the first optical filter 20 is substantially transmissive (e.g., optical transmittance≥60%) at the converted wavelength 41 and is substantially reflective (e.g., optical reflectance≥70%) at the excitation wavelength 31. Therefore, for at least one of the excitation and converted wavelengths 31, 41, the first optical filter 20 may change from being substantially transmissive to being substantially reflective when the incident angle corresponding to the at least one of the excitation and converted wavelengths 31, 41 changes to the incident angle corresponding to the other one of the excitation and converted wavelengths 31, 41.

In the illustrated embodiment of FIG. 5A, for the second incident angle α2, the optical transmittance of the plurality of microlayers versus wavelength 84 includes a transmission band edge 88 disposed between the first and second wavelengths 31, 41. At the second incident angle α2, the first optical filter 20 has an optical transmittance of at least about 60% for at least one wavelength in the transmission band edge 88. In some embodiments, at the second incident angle α2, the first optical filter 20 has an optical transmittance of at least about 70%, at least about 80%, or at least about 90% for at least one wavelength in the transmission band edge 88.

In some embodiments, for the first optical filter 20, the optical transmittance can be interchangeably referred to as a second optical property. The second optical property of the optical filter 20 has first and second values at the respective first and second wavelengths 31, 41. The first value is different from the second value by at least a factor of 2. In some embodiments, the first value is different from the second value by at least a factor of 10, at least a factor of 25, at least a factor of 50, at least a factor of 75, or at least a factor of 100.

At the first incident angle α1, the optical transmittance of the first optical filter 20 has a first value equal to T1≥60% at the excitation wavelength 31, and a second value equal to S2≤30% at the converted wavelength 41. Therefore, the first value of the optical transmittance is different from the second value of the optical transmittance by at least the factor of 2.

At the second incident angle α2, the optical transmittance of the first optical filter 20 has a first value equal to S1≤30% at the excitation wavelength 31, and a second value equal to T2≥60% at the converted wavelength 41. Therefore, the first value of the optical transmittance is different from the second value of the optical transmittance by at least the factor of 2.

In some embodiments, at the first incident angle α1, the first value of the optical transmittance equals T1 at the excitation wavelength 31. In some embodiments, the first value of the optical transmittance can be interchangeably referred to as a first transmittance of the optical filter 20 at the first wavelength 31 and at the first incident angle α1. In some embodiments, at the first incident angle α1, the second value of the optical transmittance equals S2 at the converted wavelength 41. In some embodiments, the second value of the optical transmittance can be interchangeably referred to as a second transmittance of the optical filter 20 at the second wavelength 41 and at the first incident angle α1.

The first transmittance of the optical filter 20 is equal to T1 at the first incident angle α1 and at the excitation wavelength 31. Further, the second transmittance of the optical filter 20 is equal to S2 at the first incident angle α1 and at the converted wavelength 41. Therefore, in some embodiments, at the first incident angle α1, the optical filter 20 includes different first and second transmittances (equal to T1 and S2, respectively) at the respective first and second wavelengths 31, 41.

In some embodiments, at the second incident angle α2, the first value of the optical transmittance equals S1 at the excitation wavelength 31. In some embodiments, the first value of the optical transmittance can be interchangeably referred to as a first transmittance of the optical filter 20 at the first wavelength 31 and at the second incident angle α2. In some embodiments, at the second incident angle α2, the second value of the optical transmittance equals T2 at the converted wavelength 41. In some embodiments, the second value of the optical transmittance can be interchangeably referred to as a second transmittance of the optical filter 20 at the second wavelength 41 and at the second incident angle α2.

The first transmittance of the optical filter 20 is equal to S1 at the second incident angle α2 and at the excitation wavelength 31. Further, the second transmittance of the optical filter 20 is equal to T2 at the second incident angle α2 and at the converted wavelength 41. Therefore, in some embodiments, at the second incident angle α2, the optical filter 20 includes different first and second transmittances (equal to S1 and T2, respectively) at the respective first and second wavelengths 31, 41.

In some embodiments, the first optical filter 20 is embedded in the test sample 10 of the optical stack 200. In some embodiments, the first optical filter 20 is interchangeably referred to as "the embedded first optical filter 20" when referring to the embedded design of the first optical filter 20. The embedded first optical filter 20 may be integrally manufactured with the test sample 10 by various methods, such as co-extrusion. In the embedded design, the first bonding layer 50 (shown in FIG. 1A) between the first optical filter 20 and the test sample 10 may be absent. In some embodiments, a multilayer configuration of the embedded first optical filter 20 may be substantially similar to a multilayer configuration of the first optical filter 20 shown in FIG. 3. The embedded first optical filter 20 may therefore include the plurality of microlayers 15.

Figure 5B:
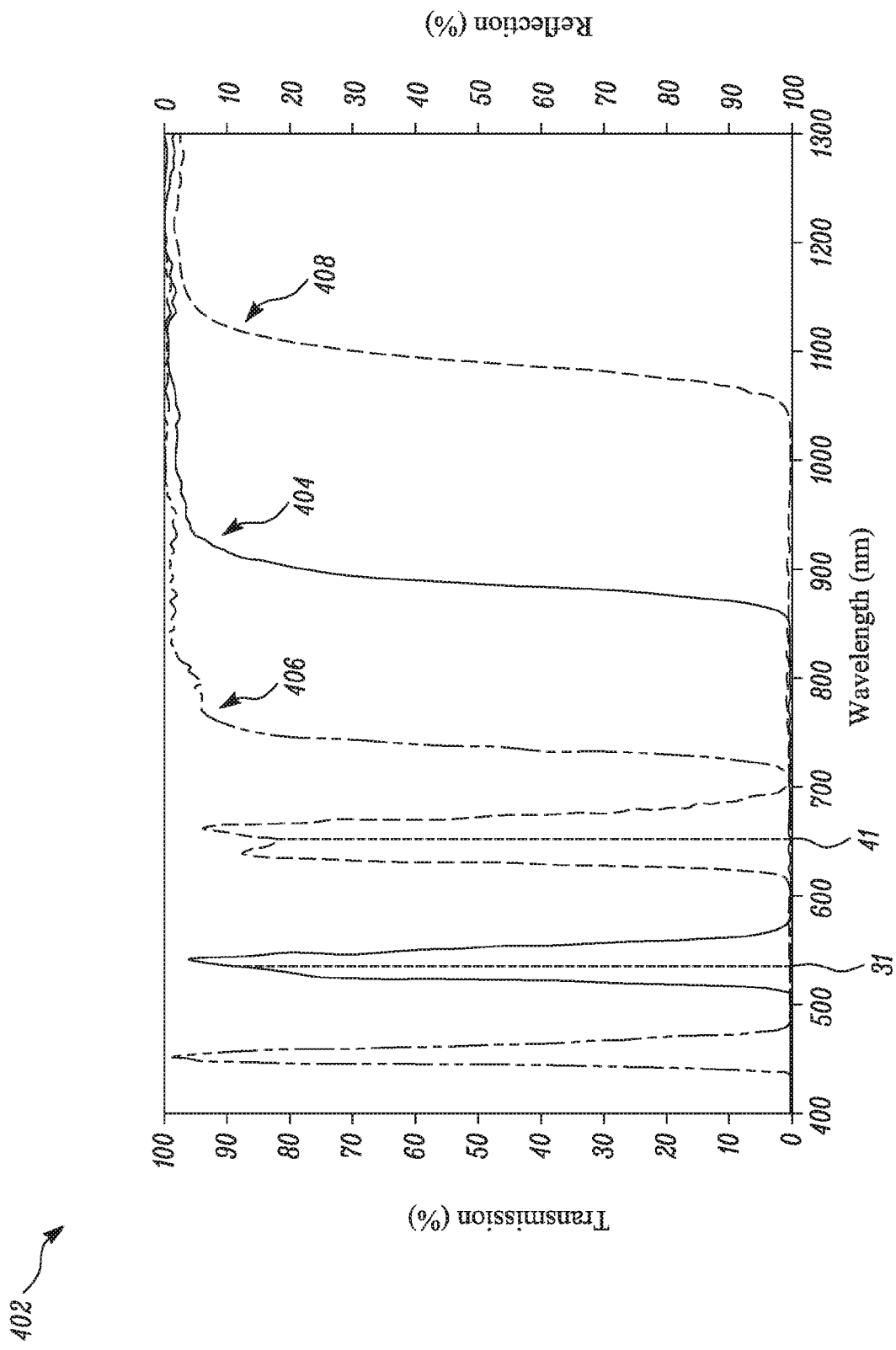
FIG. 5B is a graph illustrating transmission versus wavelength for the first optical filter embedded in a test sample of the optical stack of FIGS. 1A and 1B, according to an embodiment of the present disclosure.

FIG. 5B illustrates an exemplary graph 402 depicting transmission percentage versus wavelength for the embedded first optical filter 20. Wavelength is expressed in nanometers (nm) in the abscissa. Transmission is expressed as transmission percentage in the left ordinate. Reflection is expressed as reflection percentage in the right ordinate. The reflection percentage is complementary to the transmission percentage, i.e., reflection percentage=(100−transmission percentage).

In the illustrated embodiment of FIG. 5B, the embedded first optical filter 20 has an optical transmittance versus wavelength 406 for the first incident angle α1 of about 55 degrees. The optical transmittance versus wavelength 406 therefore illustrates a variation of the optical transmittance of the plurality of microlayers 15 of the embedded first optical filter 20 with wavelength for the first incident angle α1. Referring to the optical transmittance versus wavelength 406, for the first incident angle α1 of about 55 degrees, the embedded first optical filter 20 has an optical transmittance less than about 10% at each of the excitation and converted wavelengths 31, 41. For an intermediate incident angle of about 40 degrees, the embedded first optical filter 20 has an optical transmittance versus wavelength 404. The intermediate incident angle is between the first and second incident angles α1, α2. The optical transmittance versus wavelength 404 therefore illustrates a variation of the optical transmittance of the plurality of microlayers 15 of the embedded first optical filter 20 with wavelength for the intermediate incident angle of about 40 degrees. Referring to the optical transmittance versus wavelength 404, for the intermediate incident angle of about 40 degrees, the embedded first optical filter 20 has an optical transmittance greater than about 60% at the excitation wavelength 31, and an optical transmittance less than about 10% at the converted wavelength 41. For the second incident angle α2 of about 0 degree to about 5 degrees, the embedded first optical filter 20 has an optical transmittance versus wavelength 408. The optical transmittance versus wavelength 408 therefore illustrates a variation of the optical transmittance of the plurality of microlayers 15 of the embedded first optical filter 20 with wavelength for the second incident angle α2. Referring to the optical transmittance versus wavelength 408, for the second incident angle α2 of about 0 degree to about 5 degrees, the embedded first optical filter 20 has an optical transmittance less than about 10% at the excitation wavelength 31, and an optical transmittance greater than about 60% at the converted wavelength 41.

Therefore, the transmission percentage versus wavelength of the first optical filter 20 may be changed when embedded in the test sample 10 of the optical stack 200. For example, referring to the graphs 401, 402 shown in FIGS. 5A and 5B, respectively, the embedded first optical filter 20 may exhibit a relatively greater shift in optical transmittance toward a blue end of the visible light spectrum with an increase in angle of incidence from normal incidence as compared to a non-embedded or stacked configuration of the first optical filter 20. Specifically, referring to the optical transmittances versus wavelength 80, 406 in the graphs 401, 402, respectively, the embedded first optical filter 20 may exhibit a relatively greater shift in optical transmittance versus wavelength at the oblique first incident angle α1. In some cases, for a given oblique angle of incidence greater than about 30 degrees, an optical transmittance versus wavelength of the embedded optical filter 20 may be shifted toward the blue end of the visible spectrum by a greater degree as compared to a corresponding optical transmittance versus wavelength of the stacked configuration of the optical filter 20.

Figure 6A:
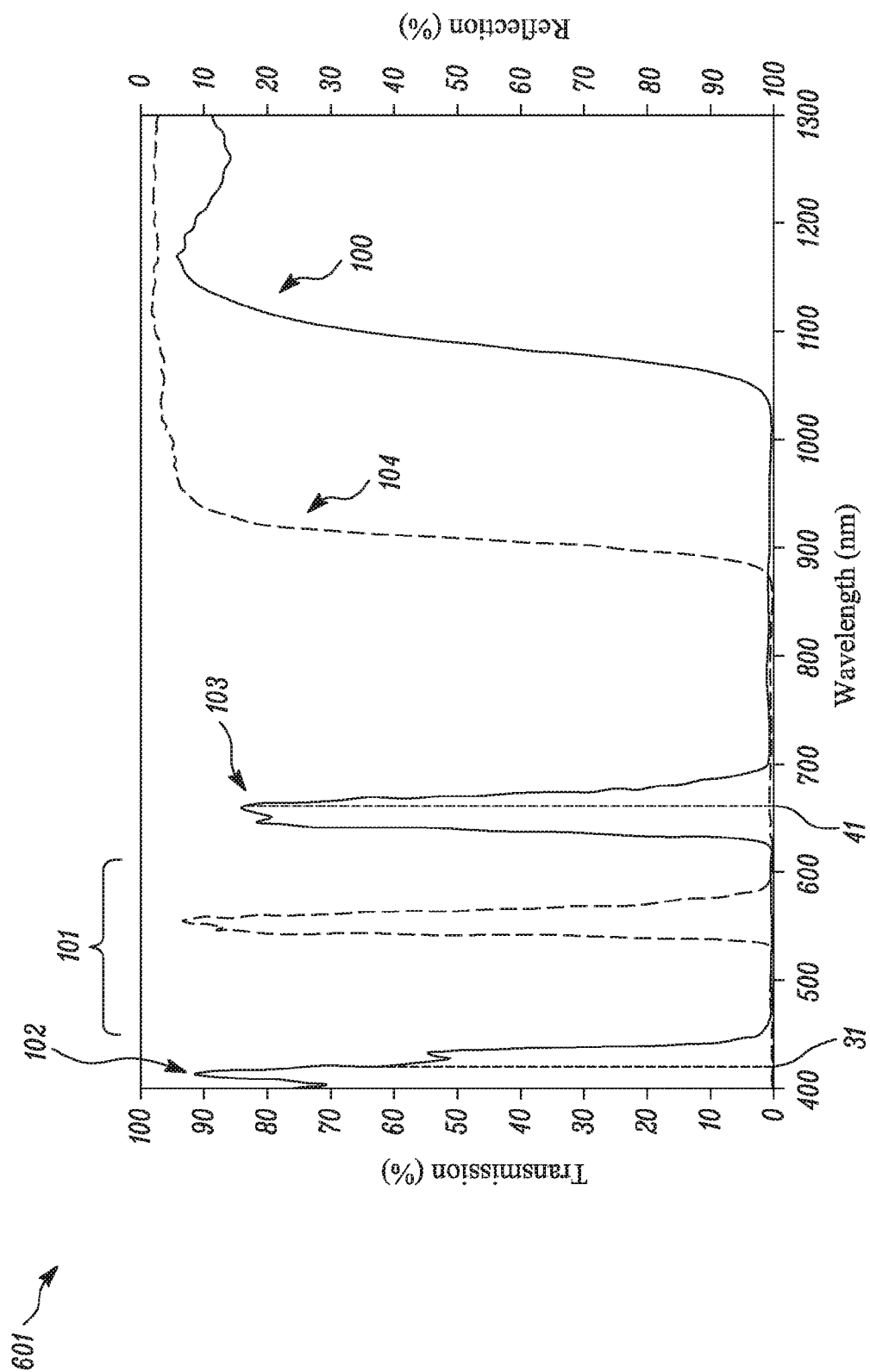
FIG. 6A is another graph illustrating transmission versus wavelength for the first optical filter, according to an embodiment of the present disclosure.

FIG. 6A illustrates an exemplary graph 601 depicting transmission percentage versus wavelength for a different configuration of the first optical filter 20. The configuration of the first optical filter 20 corresponding to FIG. 6A may be different from the configuration corresponding to FIG. 5A. The transmission percentage is provided for different values of incident angles. Wavelength is expressed in nanometers (nm) in the abscissa. Transmission is expressed as transmission percentage in the left ordinate. Reflection is expressed as reflection percentage in the right ordinate. The reflection percentage is complementary to the transmission percentage, i.e., reflection percentage=(100−transmission percentage).

In some embodiments, the first and second incident angles α1, α2 are within about 10 degrees of each other. In some embodiments, the first and second incident angles α1, α2 are within about 8 degrees, about 6 degrees, about 4 degrees, about 2 degrees, or about 1 degree of each other. Further, each of the first and second incident angles α1, α2 is less than about 10 degrees. In some embodiments, each of the first and second incident angles α1, α2 is less than about 5 degrees. Thus, in some embodiments, for the graph 601, the first incident angle α1 is substantially equal to the second incident angle α2. In the illustrated embodiment shown in the graph 601, the second incident angle α2 is less than about 10 degrees. In some embodiments, the second incident angle α2 is less than about 5 degrees.

Referring to FIGS. 4 and 6A, in some embodiments, the light source 90 is configured to emit the incident excitation light 30 having the excitation wavelength 31 and incident on the first optical filter 20 at the second incident angle α2. The test sample 10 converts at least a portion of the incident excitation light 30 to the converted light 40 at least after at least a portion of the incident excitation light 30 is transmitted by the first optical filter 20. At least a portion of the converted light 40 exits the optical stack 200 after at least a portion of the converted light 40 is transmitted by the first optical filter 20 at the second incident angle α2.

For the second incident angle α2, an optical transmittance of the plurality of microlayers versus wavelength 100 includes a lower transmission band 101 separating first and second higher transmission bands 102, 103. The optical transmittance of the plurality of microlayers versus wavelength 100 is interchangeably referred to as "the optical transmittance versus wavelength 100". The optical transmittance versus wavelength 100 therefore illustrates a variation of the optical transmittance of the plurality of microlayers 15 of the first optical filter with wavelength for the second incident angle α2. The first higher transmission band 102 includes the excitation wavelength 31 and the second higher transmission band 103 includes the converted wavelength 41. In some embodiments, the first higher transmission band 102 includes shorter wavelengths and the second higher transmission band 103 includes longer wavelengths. Specifically, the first higher transmission band 102 includes the blue wavelengths. Further, the first higher transmission band 102 provides an optical transmittance greater than about 30% for the incident excitation light 30 having the excitation wavelength 31. Further, considering the first higher transmission band 102, the plurality of microlayers 15 transmits greater than about 30% of the incident excitation light 30 having a UV wavelength range extending from about 410 nm to about 420 nm. The second higher transmission band 103 includes red wavelengths. Further, the second higher transmission band 103 provides an optical transmittance greater than about 40% for the converted light 40 having the converted wavelength 41.

With continued reference to the graph 601, for the first incident angle of about 55 degrees, the first optical filter 20 includes an optical transmittance versus wavelength 104. Referring to the optical transmittance versus wavelength 104, the first optical filter 20 has an optical transmittance less than 10% at each of the excitation and converted wavelengths 31, 41.

Figure 6B:
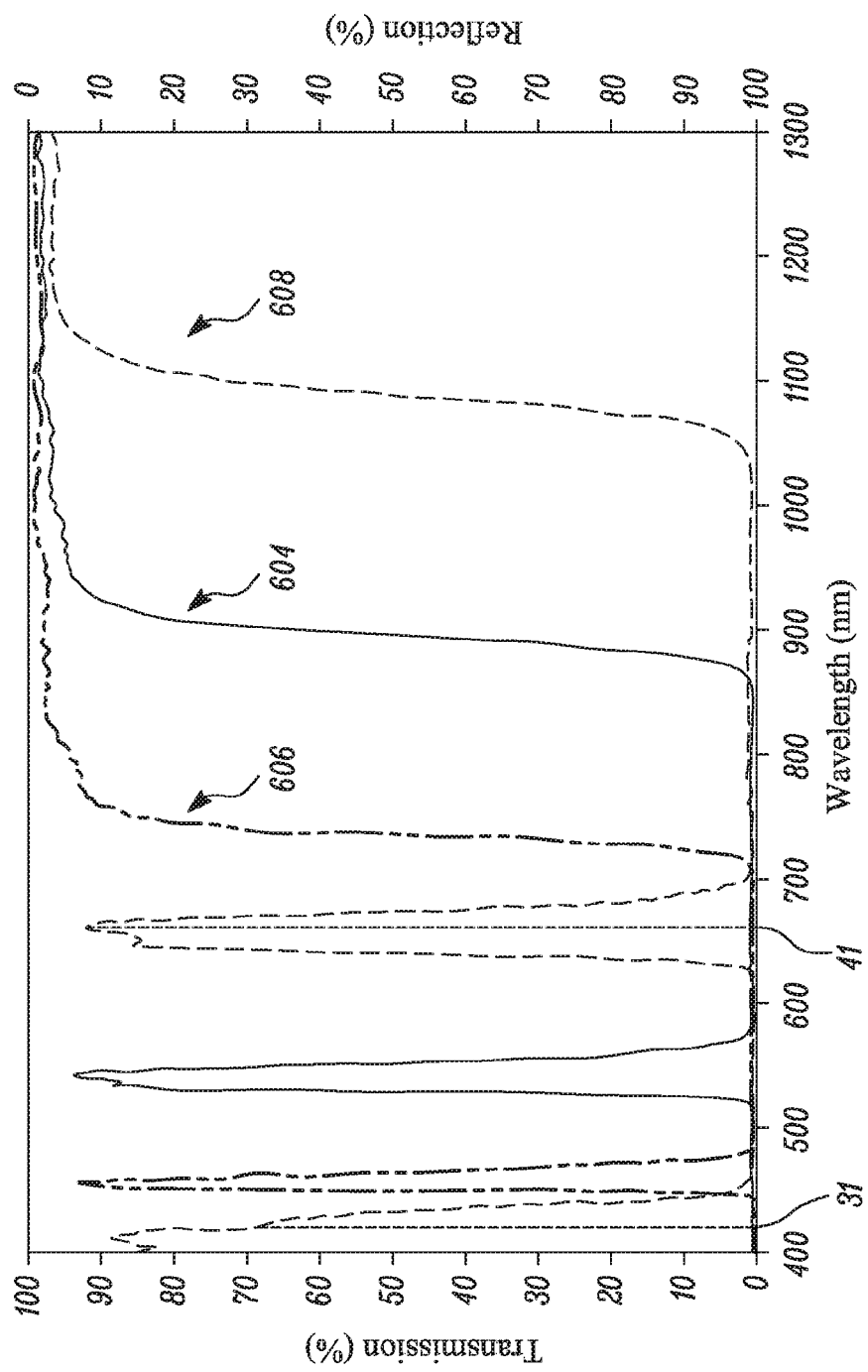
FIG. 6B is another graph illustrating transmission versus wavelength for the first optical filter embedded in the test sample, according to an embodiment of the present disclosure.

FIG. 6B illustrates an exemplary graph 602 depicting transmission percentage versus wavelength for the embedded first optical filter 20. A multilayer configuration of the embedded first optical filter 20 corresponding to the graph 602 is similar to a multilayer configuration of the first optical filter 20 corresponding to the graph 601 shown in FIG. 6A. However, the multilayer configuration of the embedded first optical filter 20 corresponding to the graph 602 is embedded as opposed to the stacked configuration of the first optical filter 20 corresponding to the graph 601.

For the first incident angle α1 of about 55 degrees, the embedded first optical filter 20 has an optical transmittance versus wavelength 606. Referring to the optical transmittance versus wavelength 606, for the first incident angle α1, the embedded first optical filter 20 has an optical transmittance less than about 10% at each of the excitation and converted wavelengths 31, 41. For an intermediate incident angle of about 40 degrees, the embedded first optical filter 20 has an optical transmittance versus wavelength 604. The intermediate incident angle is between the first and second incident angles α1, α2. Referring to the optical transmittance versus wavelength 604, the embedded first optical filter 20 has an optical transmittance less than about 10% at each of the excitation and converted wavelengths 31, 41. For the second incident angle α2 of about 0 degree to about 5 degrees, the embedded first optical filter 20 has an optical transmittance versus wavelength 608. Referring to the optical transmittance versus wavelength 608, the embedded first optical filter 20 has an optical transmittance greater than about 50% at each of the excitation and converted wavelengths 31, 41.

Referring to the graphs 601, 602 shown in FIGS. 6A and 6B, respectively, the embedded first optical filter 20 may exhibit has a relatively greater shift in optical transmittance toward a blue end of visible light spectrum with an increase in angle of incidence from normal incidence as compared to the stacked configuration of the first optical filter 20. Specifically, referring to the optical transmittances versus wavelength 104, 606 in the graphs 601, 602, respectively, the embedded first optical filter 20 may exhibit a relatively greater shift in the optical transmittance versus wavelength at the oblique first incident angle α1.

Figure 7:
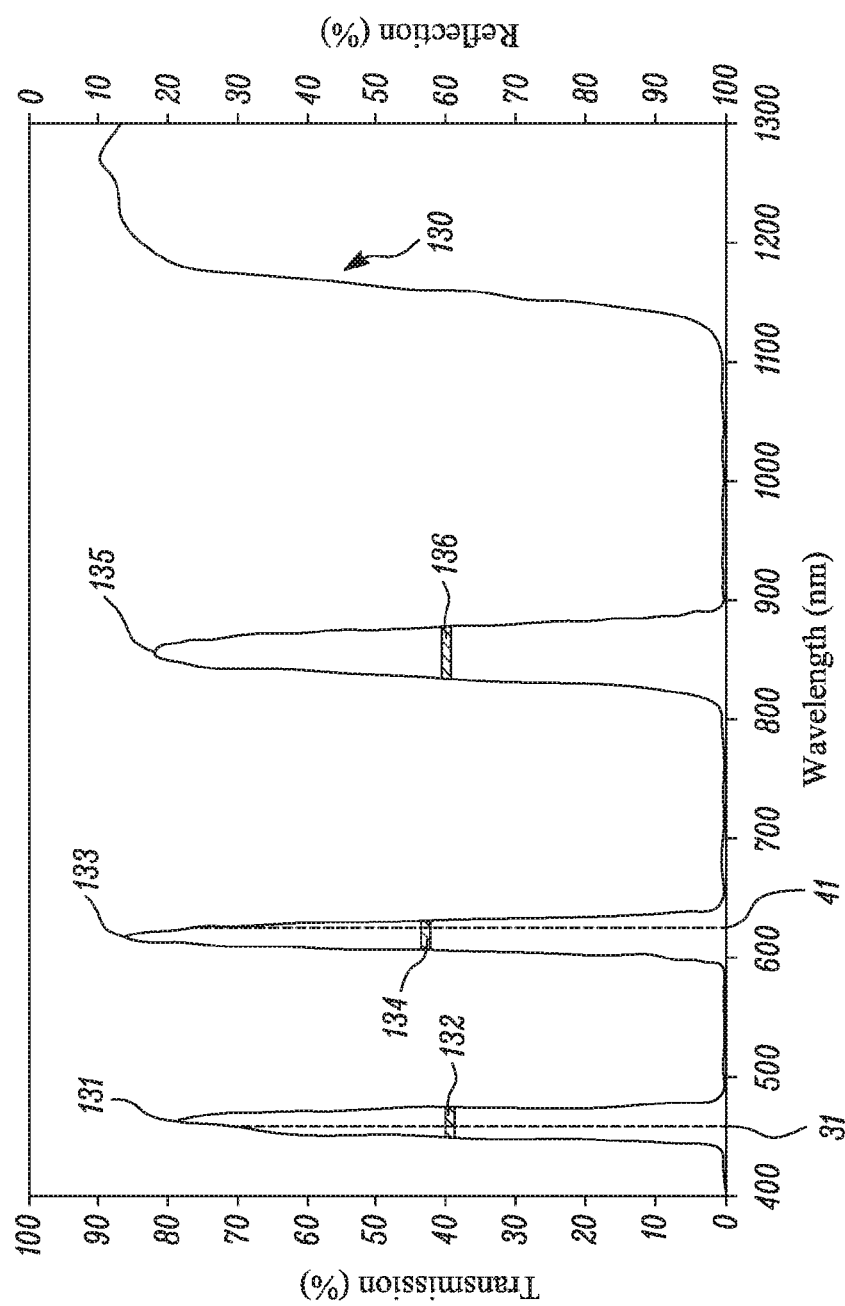
FIG. 7 is another graph illustrating transmission versus wavelength for the first optical filter, according to an embodiment of the present disclosure.

FIG. 7 illustrates an exemplary graph 701 depicting transmission percentage versus wavelength for another different configuration of the first optical filter 20. The configuration of the first optical filter 20 corresponding to FIG. 7 may be different from the configuration corresponding to FIG. 5A. The transmission percentage is provided for different values of incident angles. Wavelength is expressed in nanometers (nm) in the abscissa. Transmission is expressed as transmission percentage in the left ordinate. Reflection is expressed as reflection percentage in the right ordinate. The reflection percentage is complementary to the transmission percentage, i.e., reflection percentage=(100−transmission percentage).

In the illustrated embodiment of FIG. 7, each of the first and second incident angles α1, a2 are within about 10 degrees of each other. In some embodiments, the first incident angle α1 is substantially equal to the second incident angle α2. In the illustrated embodiment shown in the graph 701, the second incident angle α2 is less than about 10 degrees. In some embodiments, the second incident angle α2 is less than about 5 degrees.

Referring to FIG. 7, for the second incident angle α2, an optical transmittance of the plurality of microlayers versus wavelength 130 includes at least a first peak 131 with a corresponding first FWHM 132 that includes the excitation wavelength 31, but not the converted wavelength 41, and a second peak 133 with a corresponding second FWHM 134 that includes the converted wavelength 41, but not the excitation wavelength 31. The optical transmittance of the plurality of microlayers versus wavelength 130 is interchangeably referred to as "the optical transmittance versus wavelength 130". The optical transmittance versus wavelength 130 therefore illustrates a variation of the optical transmittance of the plurality of microlayers 15 of the first optical filter 20 with wavelength for the second incident angle α2.

In some embodiments, each of the first and second FWHMs 132, 134 is less than 200 nm wide. In some embodiments, each of the first and second FWHMs 132, 134 may be less than 150 nm, 100 nm, or 75 nm wide.

In some embodiments, the at least first and second peaks 131, 133 are at least 50 nm apart. In some embodiments, the at least first and second peaks 131, 133 may be at least 75 nm, or 100 nm apart. In the illustrated embodiment of FIG. 7, the first peak 131 is at a wavelength within a wavelength range from about 430 nm to about 490 nm, and the second peak 133 is at a wavelength within a wavelength range from about 590 nm to about 650 nm. Therefore, in some embodiments, the first peak 131 is at a blue wavelength and the second peak 133 is at a red wavelength.

Moreover, the at least first and second peaks 131, 133 further includes a third peak 135 with a corresponding third FWHM 136 that does not include either the converted or the excitation wavelengths 41, 31. In some embodiments, the optical transmittance versus wavelength 130 includes the third peak 135 with the corresponding third FWHM 136 that does not include either the converted or the excitation wavelengths 41, 31. In some embodiments, the third peak 135 is at an infrared wavelength. In some embodiments, the third peak 135 is at a wavelength within a wavelength range from about 820 nm to about 880 nm. The third peak 135 with the corresponding third FWHM 136 may provide the optical stack 200 and the optical device 300 with an additional analytical window. In some cases, the third peak 135 can be utilized for monitoring different health and body parameters, or for sensing various analytes.

Figure 8A:
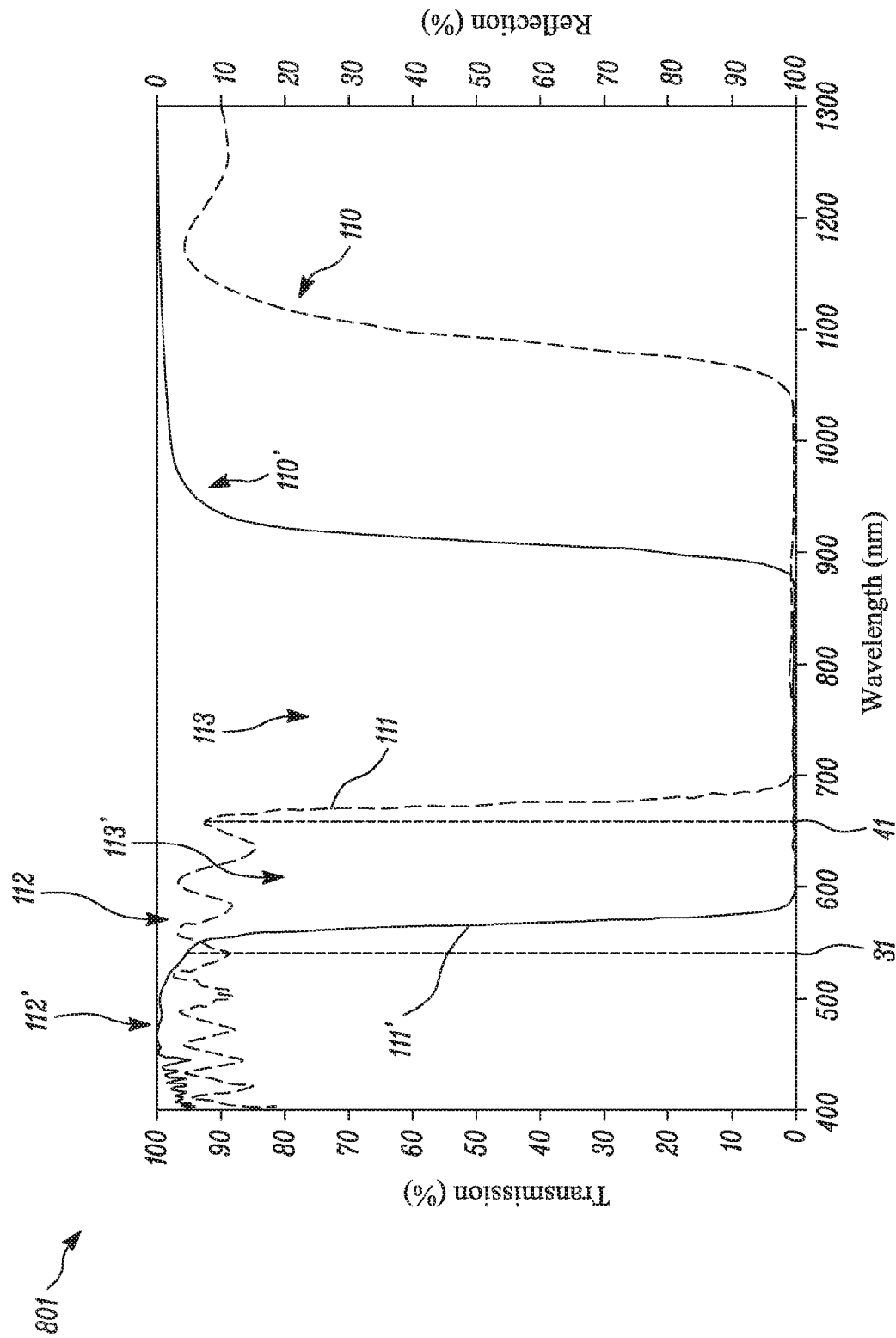
FIG. 8A is another graph illustrating transmission versus wavelength for the first optical filter, according to an embodiment of the present disclosure.

FIG. 8A illustrates an exemplary graph 801 depicting transmission percentage versus wavelength for another different configuration of the first optical filter 20. The configuration of the first optical filter 20 corresponding to FIG. 8A may be different from the configuration corresponding to FIG. 5A. The transmission percentage is provided for different values of incident angles. Wavelength is expressed in nanometers (nm) in the abscissa. Transmission is expressed as transmission percentage in the left ordinate. Reflection is expressed as reflection percentage in the right ordinate. The reflection percentage is complementary to the transmission percentage, i.e., reflection percentage=(100−transmission percentage).

Referring to the graph 801, in some embodiments, the first and second incident angles α1, α2 are within about 10 degrees of each other. In some embodiments, the first and second incident angles α1, a2 are within about 8 degrees, about 6 degrees, about 4 degrees, about 2 degrees, or about 1 degree of each other.

For the second incident angle α2 less than 10 degrees, an optical transmittance of the plurality of microlayers versus wavelength 110 includes a band edge 111 separating a higher transmission band 112 including shorter wavelengths from a lower transmission band 113 including longer wavelengths. The optical transmittance of the plurality of microlayers versus wavelength 110 is interchangeably referred to as "the optical transmittance versus wavelength 110". The optical transmittance versus wavelength 110 therefore illustrates a variation of the optical transmittance of the plurality of microlayers 15 of the first optical filter 20 with wavelength for the second incident angle α2. For the second incident angle α2 and in the higher transmission band 112, the first optical filter 20 has an optical transmittance of at least 70% in a wavelength range from about 400 nm to about 650 nm. For the second incident angle α2 and in the lower transmission band 113, the first optical filter 20 has an optical reflectance of at least 70% in the infrared region extending from about 700 nm to about 1050 nm. The higher transmission band 112 includes the excitation and the converted wavelengths 31, 41.

The graph 801 further illustrates an optical transmittance of the plurality of microlayers versus wavelength 110' for an oblique second incident angle α2 of about 55 degrees. The optical transmittance of the plurality of microlayers versus wavelength 110' is interchangeably referred to as the optical transmittance versus wavelength 110'. The optical transmittance versus wavelength 110' therefore illustrates a variation of the optical transmittance of the plurality of microlayers 15 of the first optical filter 20 with wavelength for the oblique second incident angle α2 of about 55 degrees. In some embodiments, the oblique second incident angle α2 may be any angle between 45 degrees and 60 degrees. Referring to the optical transmittances versus wavelength 110, 110', increasing the second incident angle α2 by less than about 60 degrees, shifts the higher and lower transmission bands 112, 113 so that the higher transmission band 112 includes the excitation wavelength 31 and the lower transmission band 113 includes the converted wavelength 41. Specifically, increasing the second incident angle α2 by less than about 60 degrees, shifts the higher transmission band 112 to a shifted higher transmission band 112', the lower band 113 to a shifted lower transmission band 113', and the band edge 111 to a shifted band edge 111'. The shifted higher and lower transmission bands 112', 113' include the excitation and converted wavelengths 31, 41, respectively.

Figure 8B:
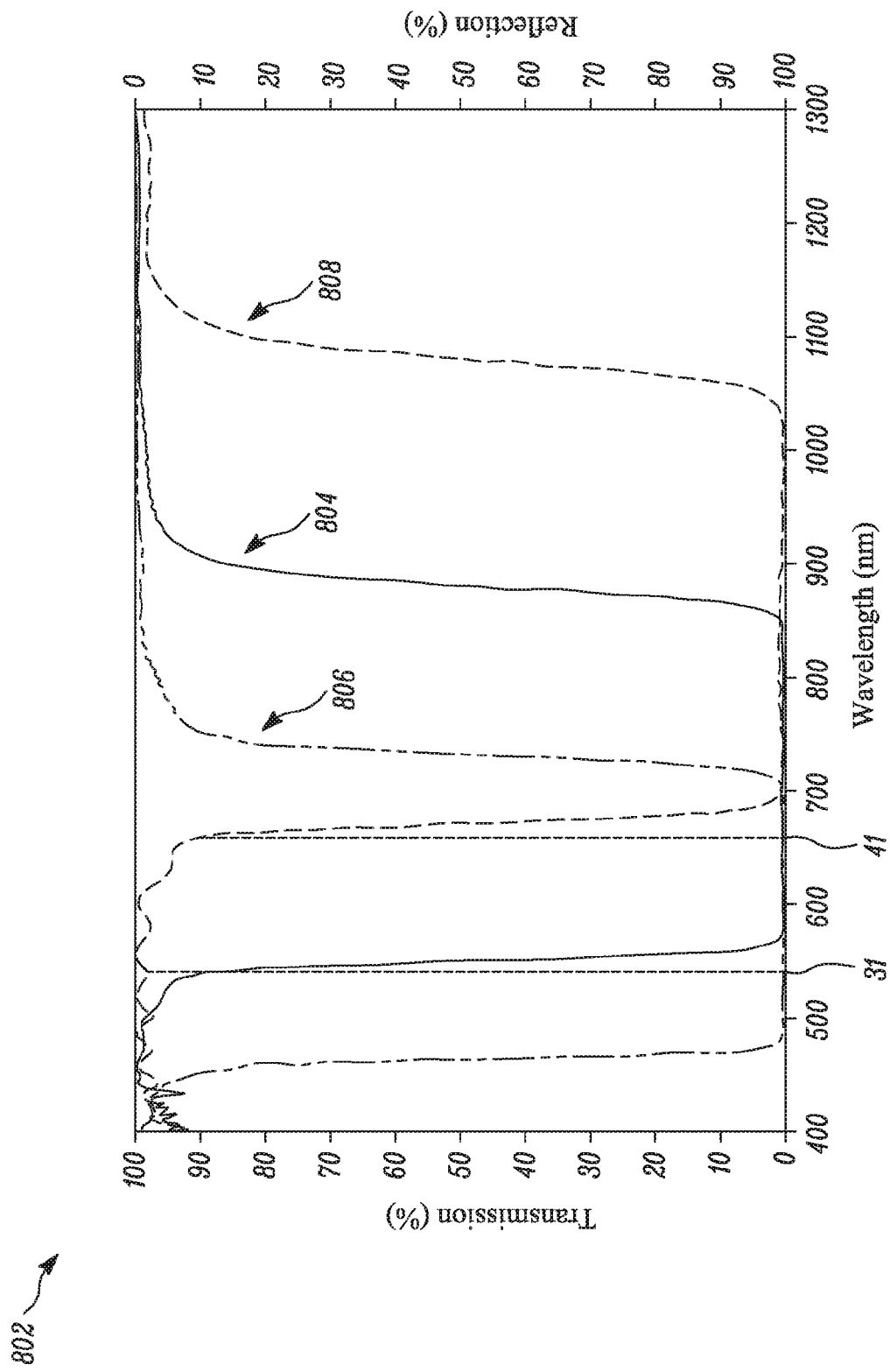
FIG. 8B is another graph illustrating transmission versus wavelength for the first optical filter embedded in the test sample, according to an embodiment of the present disclosure.

FIG. 8B illustrates an exemplary graph 802 depicting the transmission percentage versus wavelength for the embedded first optical filter 20. The multilayer configuration of the embedded first optical filter 20 corresponding to the graph 802 is similar to the multilayer configuration of the first optical filter 20 corresponding to the graph 801 shown in FIG. 8A. However, the multilayer configuration of the embedded first optical filter 20 corresponding to the graph 802 is embedded as opposed to the stacked configuration of the first optical filter 20 corresponding to the graph 801.

For the second incident angle α2 of about 55 degrees, the embedded first optical filter 20 has an optical transmittance versus wavelength 806. Referring to the optical transmittance versus wavelength 806, for second incident angle α2, the embedded first optical filter 20 has an optical transmittance less than about 10% at each of the excitation and converted wavelengths 31, 41. For an intermediate incident angle of about 40 degrees, the embedded first optical filter has an optical transmittance versus wavelength 804. Referring to the optical transmittance versus wavelength 804, the embedded first optical filter 20 has an optical transmittance greater than about 50% at the excitation wavelength 31, and less than about 10% at the converted wavelength 41. For the second incident angle α2 of about 0 degree to about 5 degrees, the embedded first optical filter 20 has an optical transmittance versus wavelength 808. Referring to the optical transmittance versus wavelength 808, the embedded first optical filter 20 has an optical transmittance greater than about 60% at each of the excitation and converted wavelengths 31, 41.

Referring to the graphs 801, 802 shown in FIGS. 8A and 8B, respectively, the embedded first optical filter 20 may exhibit a relatively greater shift in optical transmittance toward the blue end of visible light spectrum with an increase in angle of incidence from normal incidence as compared to the stacked configuration of the first optical filter 20. Specifically, referring to the optical transmittances versus wavelength 110', 806 in the graphs 801, 802, respectively, the embedded first optical filter 20 may exhibit a relatively greater shift in the optical transmittance versus wavelength at the oblique second incident angle α2 of about 55 degrees.

Figure 9:
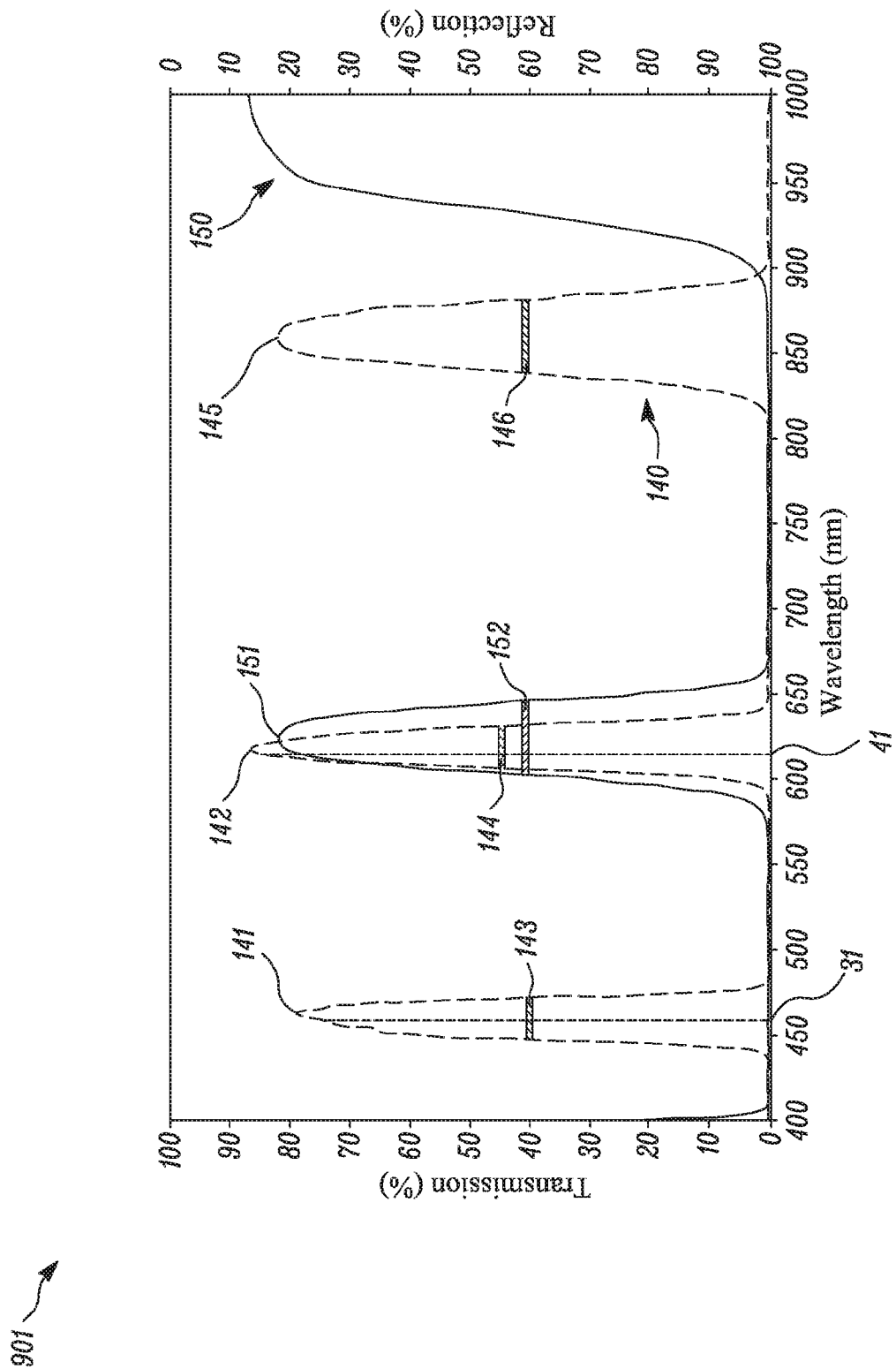
FIG. 9 is another graph illustrating transmission versus wavelength for the first optical filter, according to an embodiment of the present disclosure.

FIG. 9 illustrates an exemplary graph 901 depicting transmission percentage versus wavelength for another different configuration of the first optical filter 20. The configuration of the first optical filter 20 corresponding to FIG. 9 may be different from the configuration corresponding to FIG. 5A. Wavelength is expressed in nanometers (nm) in the abscissa. Transmission is expressed as transmission percentage in the left ordinate. Reflection is expressed as reflection percentage in the right ordinate. The reflection percentage is complementary to the transmission percentage, i.e., reflection percentage=(100–transmission percentage).

In the illustrated embodiment of FIG. 9, the first incident angle α1 is less than about 10 degrees, less than about 5 degrees, or less than about 2 degrees. The second incident angle α2 is an oblique angle of about 60 degrees, or about 55 degrees.

Referring to FIG. 9, for the first incident angle α1, an optical transmittance of the plurality of microlayers versus wavelength 140 includes at least first and second peaks 141, 142 with respective first and second FWHMs 143, 144. The optical transmittance of the plurality of microlayers versus wavelength 140 is interchangeably referred to as "the optical transmittance versus wavelength 140". The optical transmittance versus wavelength 140 therefore illustrates a variation of the optical transmittance of the plurality of microlayers 15 of the first optical filter with wavelength for the first incident angle α1.

The first FWHM 143 includes the first wavelength 31, but not the second wavelength 41. The second FWHM 144 includes the second wavelength 41, but not the first wavelength 31. In some embodiments, each of the first and second FWHMs 143, 144 is less than about 300 nm wide. In some embodiments, each of the first and second FWHMs 143, 144 may be less than about 250 nm, less than about 200 nm, less than about 150 nm, less than about 100 nm, or less than about 75 nm wide. In some embodiments, the at least first and second peaks 141, 142 are at least 100 nm apart. In some embodiments, the at least first and second peaks 141, 142 may be at least 150 nm, or at least 200 nm apart. In some embodiments, the first peak 141 is at a blue wavelength and the second peak 142 is at a red wavelength.

Moreover, in some embodiments, the at least first and second peaks 141, 142 further includes a third peak 145 with a corresponding third FWHM 146 that does not include either the second or the first wavelengths 41, 31. In some embodiments, the optical transmittance versus wavelength 140 further includes the third peak 145 with the corresponding third FWHM 146 that does not include either the second or the first wavelengths 41, 31. In some embodiments, the third peak 145 is at an infrared wavelength. In some embodiments, the third peak 145 is at a wavelength within a wavelength range from about 820 nm to about 880 nm. The third peak 145 with the corresponding third FWHM 146 may provide the optical stack 200 and the optical device 300 with an additional analytical window. In some cases, the third peak 145 can be utilized for monitoring different health and body parameters, for sensing various analytes, etc.

In some embodiments, for the different second incident angle α2, an optical transmittance of the plurality of microlayers versus wavelength 150 is less than about 10% at the first wavelength 31. The optical transmittance of the plurality of microlayers versus wavelength 150 is interchangeably referred to as "the optical transmittance versus wavelength 150". The optical transmittance versus wavelength 150 therefore illustrates a variation of the optical transmittance of the plurality of microlayers 15 of the first optical filter 20 with wavelength for the second incident angle α2. In some embodiments, the optical transmittance versus wavelength 150 is less than about 5%, less than about 2%, or less than about 1% at the first wavelength 31.

In some embodiments, the optical transmittance versus wavelength 150 includes at least a third peak 151 with a corresponding third FWHM 152 that includes the second wavelength 41, and does not include the first wavelength 31. In some embodiments, the third FWHM 152 is less than about 300 nm wide. In some embodiments, the third FWHM 152 may be less than about 200 nm, less than about 150 nm, or less than about 100 nm wide. The third peak 151 is at a red wavelength.

Referring to FIG. 3, the first optical filter 20 is subjected to a substantially normally incident light 29. In some embodiments, the substantially normally incident light 29 may be the incident excitation light 30 (shown in FIGS. 1A and 1B) or the converted light 40 (shown in FIGS. 1A and 1B). Referring to FIGS. 1A, 1B and 3, for the substantially normally incident light 29 and for at least one wavelength in a visible wavelength range from about 420 nm to about 680 nm, the plurality of microlayers 15 transmits at least 60% of the incident light 29 having a first polarization state, and reflects at least 60% of the incident light 29 having an orthogonal second polarization state. In some embodiments, for the substantially normally incident light 29 and for the at least one wavelength in the visible wavelength range from about 420 nm to about 680 nm, the plurality of microlayers 15 transmits at least 60% of the incident light 29 for each of the mutually orthogonal first and second polarization states. In such cases where the plurality of microlayers 15 transmits at least 60% of the incident light 29 for each of the mutually orthogonal first and second polarization states, the first optical filter 20 is a partial mirror.

In some embodiments, the first polarization state is a P polarization state, and the second polarization state is a S polarization state. In some other embodiments, the first polarization state is a S polarization state, and the second polarization state is a P polarization state. In some embodiments, the first polarization state is generally along the x-axis, while the second polarization state is generally along the y-axis.

Referring again to FIGS. 1A, 1B and 3, in some embodiments, the first and second optical filters 20, 60 can be interchangeably referred to as first and second partial mirrors 20, 60. In some embodiments, the optical stack 200 can be interchangeably referred to herein as an optical construction 200. Therefore, the optical construction 200 for sensing the presence of the analyte includes the sensor material 10 disposed between the first and second partial mirrors 20, 60. In some embodiments, for the substantially normally incident light 29 and a predetermined wavelength range from about 400 nm to about 1000 nm, each of the first and second partial mirrors 20, 60 transmits at least 50% of the incident light 29 for a first wavelength (e.g., the first wavelength 31 in FIG. 5A) in the predetermined wavelength range and reflects at least 50% of the incident light 29 for a different second wavelength (e.g., the second wavelength 41 in FIG. 5A) in the predetermined wavelength range.

Figure 10:
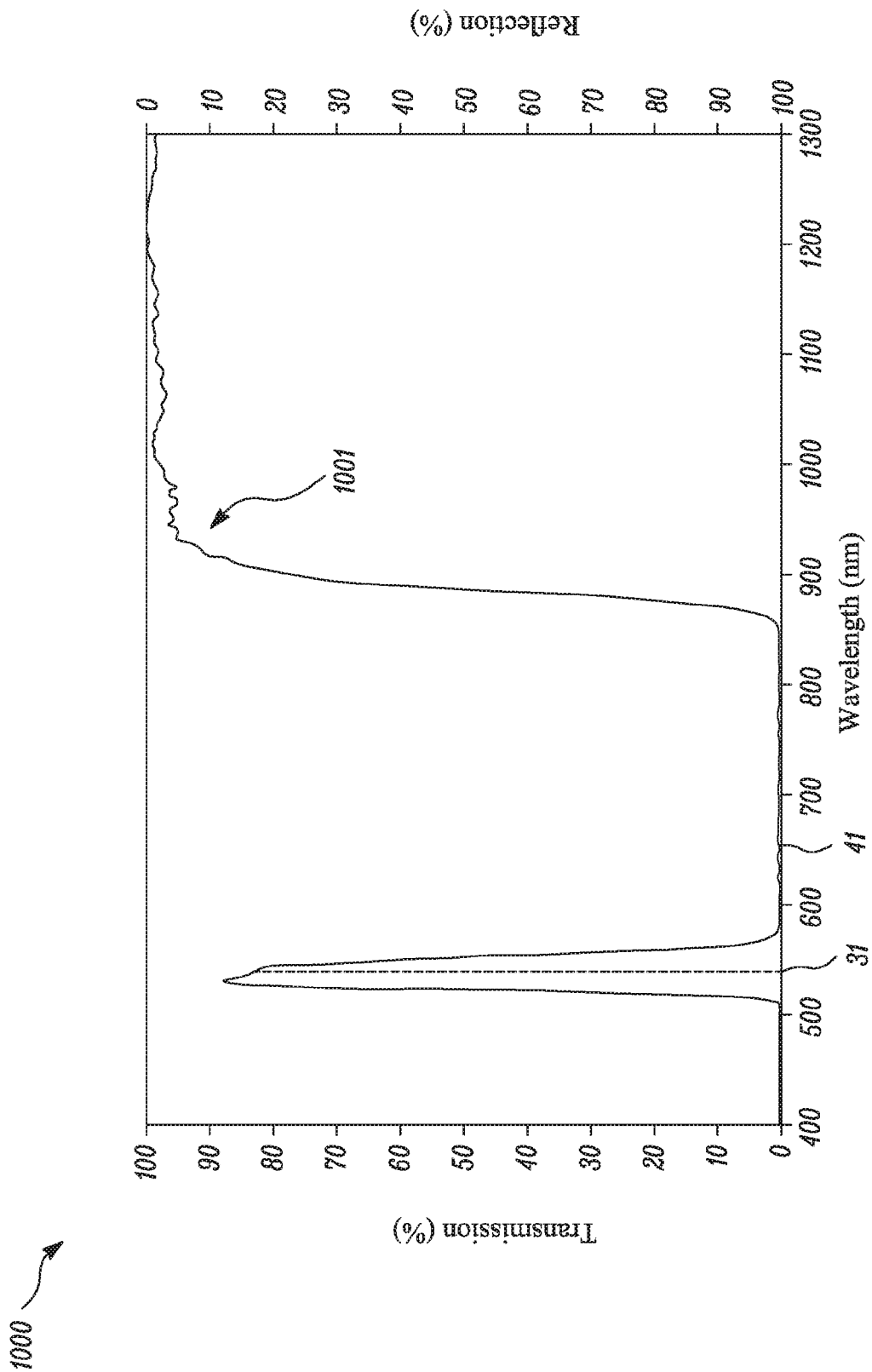
FIG. 10 is a schematic sectional view of another optical device including the optical stack of FIG. 1A, according to an embodiment of the present disclosure.

FIG. 10 illustrates an optical device 400 for sensing a presence of the analyte in the person, according to an embodiment of the present disclosure. In some embodiments, the analyte is oxygen. The optical device 400 includes the patch 200, the light source 90 and the reader 91. The patch 200 is configured to be placed on the skin 160 of the person. The reader 91 is configured to read at least one of an intensity of the second light 40 and at least an image of a portion of at least one of the sensor material 10 and the optical filter 20. In the illustrated embodiment of FIG. 10, the light source 90 and the reader 91 are disposed adjacent to the optical filter 20. In some embodiments, the reader 91 and the optical filter 20 are bonded together, for example, by means of an optical adhesive, epoxy, lamination, or any other suitable method of attachment. In some embodiments, the patch 200 includes at least one of the light source 90 and the reader 91.

Figure 11:
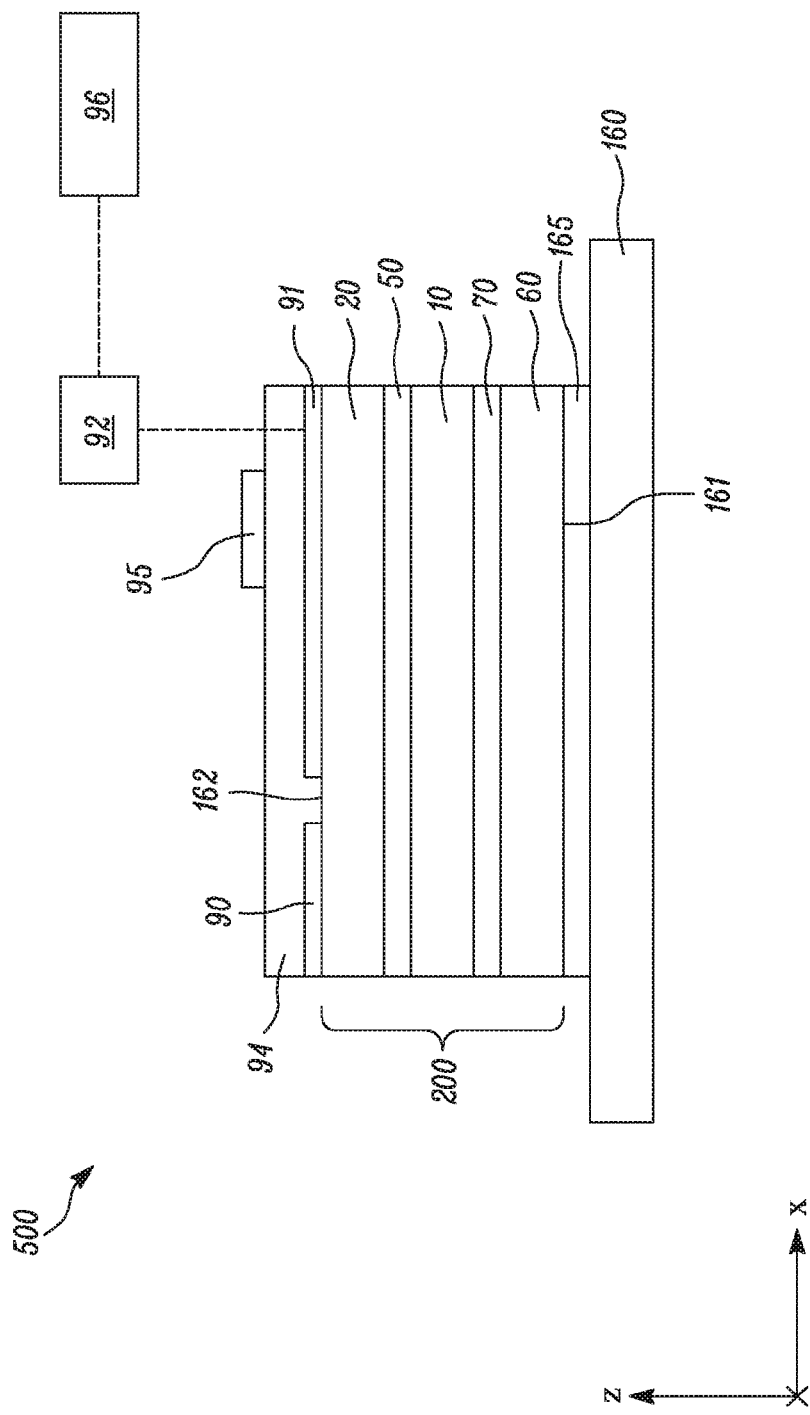
FIG. 11 is a schematic view of a reader of the optical device of FIG. 10, according to an embodiment of the present disclosure.

In some embodiments, the reader 91 includes the light source 90. The reader 91 may transform graphic indicia information patterns into electrical signals, which are decoded into alphanumerical characters with information content. These alphanumerical characters are typically represented in digital form and used as input to a data processing system for various applications. As shown in FIG. 11, the reader 91 includes a plurality of pixels 93. In some embodiments, each pixel 93 of the reader 91 detects the amount of light incident at its particular location and stores an electrical charge that varies as a function of the incident light.

In some embodiments, the optical device 400 further includes a protective layer 94 covering the at least one of the light source 90 and the reader 91. In the illustrated embodiment of FIG. 10, the protective layer 94 covers both the light source 90 and the reader 91. Further, the protective layer 94 is disposed adjacent to the optical filter 20 and opposite the sensor material 10.

In some embodiments, the patch 200 includes a bottom portion 161 and a top portion 162 opposite to the bottom portion 161. In some embodiments, the bottom portion 161 of the patch 200 is configured to face the skin 160. In some embodiments, the bottom portion 161 of the patch 200 has a greater oxygen permeability than the top portion 162 of the patch 200 configured to face away from the skin 160.

As shown in FIG. 10, the patch 200 further includes a readable indicia 95 disposed on the optical filter 20. In some embodiments, the reader 91 is configured to read the indicia 95. In some embodiments, the readable indicia 95 includes an identification indicia. In some embodiments, the readable indicia 95 may include stamps, signs, markings, labels, indications, or various identifying marks. In some embodiments, the readable indicia 95 may include a machine-readable barcode to be read by the reader 91.

In the illustrated embodiment of FIG. 10, the optical patch 200, the light source 90, the reader 91, the protective layer 94 and the readable indicia 95 are stacked together to form an optical construction 170.

In some embodiments, the optical device 400 further includes a controller 92 configured to receive information read by the reader 91. In some embodiments, the controller 92 is further configured to at least one of activate and deactivate the reader 91. In some embodiments, the controller 92 activates as well as deactivates the reader 91, as per desired application attributes. In some embodiments, the controller 92 converts analog image signals received from the pixels 93 (shown in FIG. 11) of the reader 91 into digital image data in a predetermined order, and then outputs the converted digital data. Specifically, the reader 91 reads the image data provided by the second light 40, emitted by the sensor material 10.

In some embodiments, the controller 92 communicates wirelessly with the reader 91. In some embodiments, the controller 92 is further configured to provide an audible alarm or warning in response to the received information. Specifically, the controller 92 provides the audible alarm or warning once it receives the information read by the reader 91. The warning may include a visual alarm or other form of signal. In some embodiments, the controller 92 is further configured to send at least one message to an electronic device 96 based on the received information. In some embodiments, the at least one message may include one or more text messages, instant messages, electronic mails, commands, or multiple requests. In some embodiments, the electronic device 96 includes a cell phone. In some embodiments, the electronic device 96 may include a computer, a tablet, a camera, or any electronic device having a display.

In some embodiments, a medical device includes the optical device 400. In some embodiments, a wearable device, configured to be worn by the person, includes the optical device 400. In some embodiments, the optical device 400 is substantially flexible and configured to conform to a curved surface.

Figure 12:
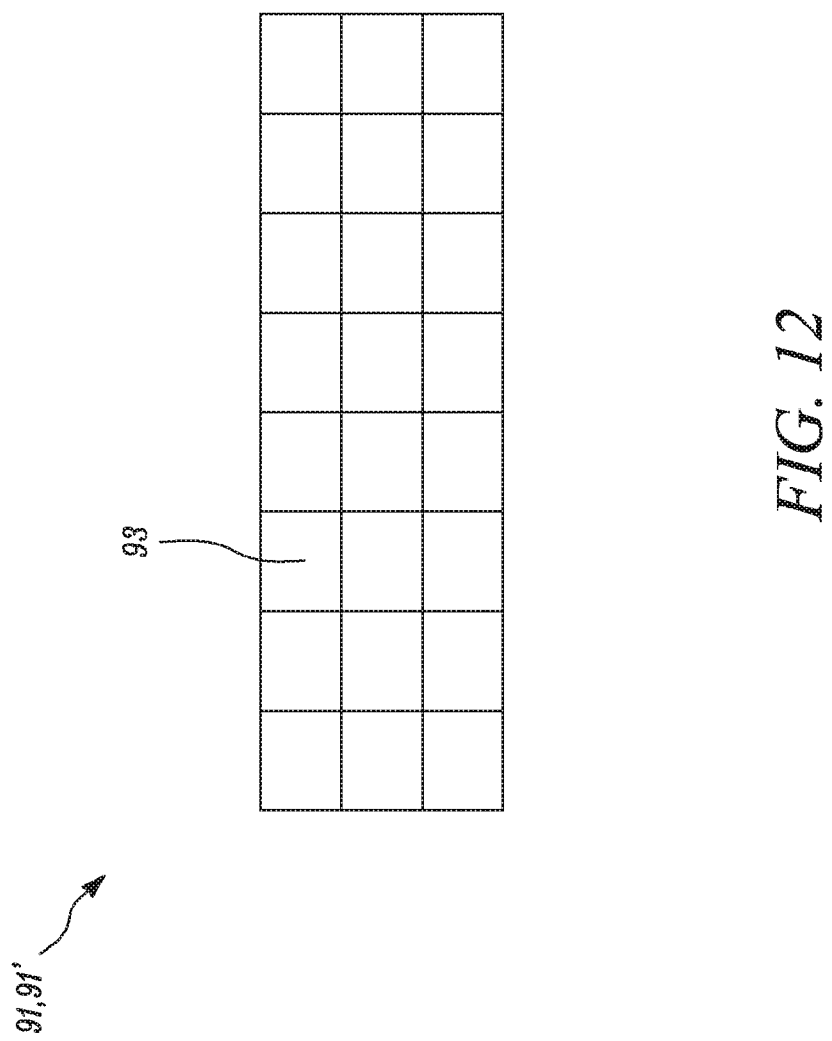
FIG. 12 is a schematic view of the first optical filter having a segmented design, according to an embodiment of the present disclosure.

FIG. 12 illustrates an optical filter 20' according to another embodiment of the present disclosure. The optical filter 20' may have a similar multilayer configuration as the optical filter of FIG. 3. However, the optical filter 20' is discontinuous including a plurality of spaced apart segments 24. In the illustrated embodiment of FIG. 12, the optical filter 20' includes a total of three spaced apart segments 24. In some embodiments, the optical filter 20' may include more than three spaced apart segments. Further, the segments 24 may have similar or different dimensions.

Figure 13:
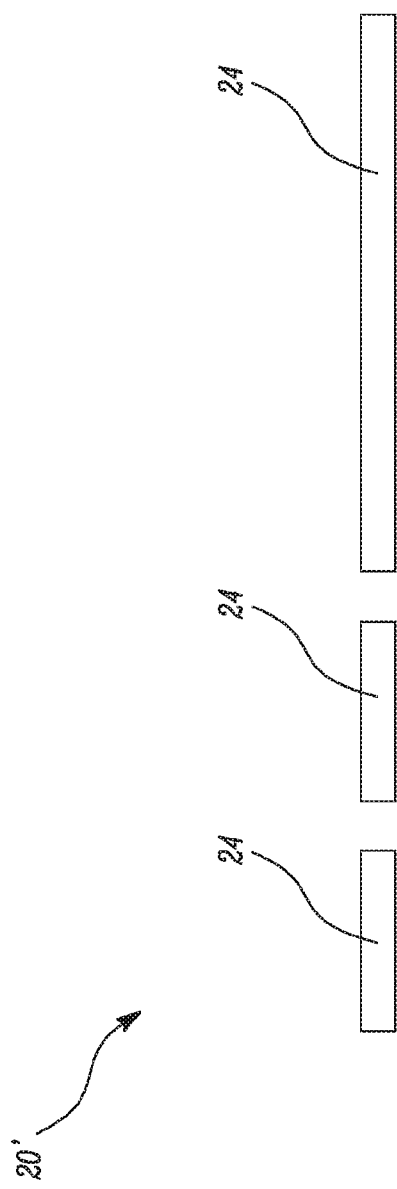
FIG. 13 is a schematic view of another optical device, according to an embodiment of the present disclosure.

FIG. 13 illustrates a schematic view of an optical device 500 according to another embodiment of the present disclosure. The optical device 500 is substantially similar to the optical device 400 illustrated in FIG. 10. Common components between the optical devices 400, 500 are illustrated by the same reference numerals. However, in the optical device 500, a reader 91' is external to the patch 200, and spaced apart from the top portion 162 of the patch 200. The construction of the reader 91' may be substantially similar to the construction of the reader 91, and hence, the reader 91' may include the plurality of pixels 93, as shown in FIG. 11. Further, the light source 90 is also external to the patch 200.

In the illustrated embodiment of FIG. 13, the optical device 500 further includes a light redirecting layer 180 for redirecting the emitted first light 30 from propagating along a first direction 181 to propagating along a different second direction 182. The sensor material 10 and the optical filter 20 are irradiated with the first light 30 at a predetermined desirable angle provided by the second direction 182 of the first light 30. In some embodiments, the light redirecting layer 180 includes a plurality of prisms 183 disposed on the protective layer 94. Generally, the light redirecting layer 180 is a thin transparent or translucent optical layer that redistributes the first light 30 passing through it such that distribution of the first light 30 exiting the light redirecting layer 180 is directed more towards the normal N. The plurality of prisms 183 changes the angle of the first light 30 exiting the light redirecting layer 180.

In the illustrated embodiment of FIG. 13, the optical patch 200, the protective layer 94 and the light redirecting layer 180 are stacked together to form an optical construction 175.

Further, the sensor material 10 is irradiated with the first light 30 at a time t0 and the reader 91 reads the second light 40 at a plurality of times between t0 and a later time t1. For example, the reading of the second light 40 at the plurality of times between the time t0 and the later time t1 may be utilized to measure a change in an intensity of the second light 40 between the time t0 and the later time t1.

In some embodiments, a medical device includes the optical device 500. In some embodiments, a wearable device, configured to be worn by the person, includes the optical device 500. In some embodiments, the optical device 500 is substantially flexible and configured to conform to a curved surface.

With reference to FIGS. 1A-13, the optical devices 300, 400, 500 including the optical stack 200 or the patch 200 may be used to sense the presence of the analyte, for example, oxygen, in a person. Specifically, the optical devices 300, 400, 500 may be used to sense oxygen in a skin tissue of the person. The optical stack 200 is irradiated with the incident excitation light 30 having the excitation wavelength 31, and substantially transmits the converted light 40 having the converted wavelength 41. In some cases, the converted wavelength 41 is a relatively longer wavelength than the excitation wavelength 31, and hence exhibits a lower energy due to the phenomenon of fluorescence. Hence, upon irradiation with the incident excitation light 30 having the excitation wavelength 31, the test sample 10 may transmit the differently colored converted light 40 having the converted wavelength 41.

The readers 91, 91' may receive the information from the converted light 40 having the converted wavelength 41, emitted by the test sample 10. Oxygen generally acts as a fluorescence quencher, therefore, the presence of oxygen may decrease an intensity of the converted light 40 which is read by the readers 91, 91'. The controller 92 may receive the information read by the reader 91, and may provide the warning or alarm to the electronic device 96 in response to the received information. For example, if the information received by the reader 91 depicts a considerable amount of reduction in the intensity of the converted light 40 between the time t0 and the later time t1, the controller 92 may provide an alarm to the electronic device 96 indicating the presence of oxygen. In another example, if the information received by the reader 91 depicts a minimal reduction in the intensity of the converted light 40 between the time t0 and the later time t1, the controller 92 may provide an alarm to the electronic device 96 indicating lower levels of oxygen. In another example, if the information received by the reader 91 depicts no reduction in the intensity of the converted light 40 between the time t0 and the later time t1, the controller 92 may provide an alarm to the electronic device 96 indicating absence of oxygen. Hence, the optical devices 300, 400, 500 including the optical stack 200 with the test sample 10 may be used to sense the presence of oxygen in the skin 160 of the person.

The test sample 10 may have to be irradiated with the incident excitation light 30 having the excitation wavelength 31 in order to initiate fluorescence. The optical filter 20 having the plurality of microlayers 15 may have a relatively high optical transmittance at the excitation wavelength 31 and at the first incident angle α1, such that at least a portion of the incident excitation light 30 having the excitation wavelength 31 is transmitted by the optical filter 20 and further irradiates the test sample 10. Also, the optical filter 20 may have a relatively high optical transmittance at the converted wavelength 41 and at the second incident angle α2, such that the converted light 40 having the converted wavelength 41 is transmitted by the optical filter 20, and the reader 91 may observe a light emitted by the test sample 10.

Hence, the optical stack 200 or a combination of the optical filter 20 and the test sample may enable the optical devices 300, 400, 500 to sense oxygen in various locations, such as skin tissues. The optical devices 300, 400, 500 may also be used to sense the presence of other analytes, for example, by varying the material of the test sample 10, as per desired applications. The optical stack 200 may allow direct sensing of oxygen in the skin tissue without relying on blood flow. Therefore, the optical stack may allow accurate sensing of oxygen. The optical stack 200 may be used as a patch that can be removably applied on the skin 160 of the person to facilitate non-invasive sensing and monitoring of oxygen levels.

Further, the change in the optical intensity of the converted light 40 with an increase in oxygen concentration may allow accurate determination of oxygen level or concentration. The optical stack 200 may also be easily used with various types of optical readers or sensors. For example, the optical stack 200 may be used with the reader 91 that is incorporated within the patch. The optical stack 200 may also be used with the reader 91' that is external to the patch. Further, various other devices, such as the controller 92, and the electronic devices 96, may be combined with the optical stack 200 as per desired application attributes. In some cases, additional layers may be combined with the optical filter. Such additional layers may include the second optical filter 60, the light redirecting layer 180, the protective layer 94, the readable indicia 95, etc.

Moreover, the optical filter 20 may ensure that the test sample 10 receives at least a portion of the incident excitation light 30 having the excitation wavelength 31 and incident at the first incident angle α1. The optical filter 20 may further ensure that at least a portion of the converted light 40 having the converted wavelength 41 and incident at the second incident angle α2 is transmitted for further analysis. Therefore, the optical filter 20 may provide both spectral filtering (based on wavelength) and spatial filtering (based on incident angle) to allow the test sample 10 to receive the incident excitation light 30 and the optical sensors or readers 91, 91' to receive the converted light 40 from the test sample 10. Additionally, the optical filter 20 may be used to substantially block light from other sources (e.g., ambient light) from reaching the test sample 10. The optical filter 20 may further substantially prevent light other than the converted light 40 from being transmitted to the readers 91, 91'. For example, in some cases, an optical transmittance of the optical filter 20 may change by at least a factor of 2 when a wavelength of an incident light changes from the excitation wavelength 31 to the converted wavelength 41 for the first incident angle α1 corresponding to the incident excitation light 30. Similarly, an optical transmittance of the optical filter may change by at least a factor of 2 when a wavelength of an incident light changes from the converted wavelength 41 to the excitation wavelength 31 for the second incident angle α2 corresponding to the converted light 40. In other words, the optical filter 20 may substantially block or reflect an incident light having the converted wavelength 41 and incident at the first incident angle α1. Similarly, the optical filter 20 may substantially block or reflect an incident light having the excitation wavelength 30 and incident at the second incident angle α2. Therefore, the optical filter 20 may be optimized for a specific combination of the excitation and converted wavelengths 31, 41, and the first and second incident angles α1, α2, and filter out other combinations of wavelengths and incident angles to allow accurate sensing of the analyte.

A design of the optical filter 20 may be conveniently varied as per various application parameters, for example, the excitation wavelength 31 and the first incident angle α1 corresponding to the incident excitation light 30, the converted wavelength 41 and the second incident angle α2 corresponding to the converted light 40, a desired thickness of the optical stack 200, a desired permeability of the analyte, etc. Various design parameters of the optical filter 20 may be changed, for example, but not limited to, the average thickness "t" of each of the first and second microlayers 21, 22, a ratio of the average thickness of the first microlayer 21 to the average thickness of the second microlayer 22, a total number of the first and second microlayers 21, 22, a thickness gradient across a length of the optical filter 20, materials of the first and second microlayers 21, 22, and so forth.

In some cases, the patch 200 including the optical filter 20 may be partially permeable to oxygen to allow ambient oxygen to reach the skin tissue in order to promote healing. However, the bottom portion 161 of the patch 200 configured to face the skin 160 may have a greater oxygen permeability than the top portion 162 of the patch 200 configured to face away from the skin 160. This may allow the test sample 10 to receive a greater amount of oxygen from the skin tissue as compared to ambient oxygen. Thus, an accuracy of oxygen sensing may not be impacted.

Unless otherwise indicated, all numbers expressing feature sizes, amounts, and physical properties used in the specification and claims are to be understood as being modified by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

The invention claimed is:

1. An optical stack comprising a test sample disposed on a first optical filter, the test sample configured to convert at least a portion of an incident excitation light having an excitation wavelength to a converted light having at least one converted wavelength different from the excitation wavelength, the first optical filter comprising a plurality of microlayers numbering at least 20 in total, each of the plurality of microlayers having an average thickness of less than about 500 nanometers (nm), such that the plurality of microlayers has:
   an optical transmittance T1>20% at the excitation wavelength and at a first incident angle;
   an optical transmittance T2>20% at the at least one converted wavelength and at a second incident angle; and
   an optical reflectance R1>40% at least one of the excitation wavelength and the at least one converted wavelength and at least one of the first incident angle and the second incident angle;
   wherein:
      for the at least one of the excitation and the at least one converted wavelength, a corresponding optical transmittance of the first optical filter changes by at least a factor of 2 when an initial incident angle corresponding to the at least one of the excitation and the at least one converted wavelength changes to the initial incident angle corresponding to the other one of the excitation and the at least one converted wavelength; and
      for the second incident angle, a microlayer optical transmittance of the plurality of microlayers versus wavelength comprises a lower transmission band separating a first higher transmission band and a second higher transmission band, the first higher transmission band comprising the excitation wavelength and the second higher transmission band comprising the at least one converted wavelength.

2. The optical stack of claim 1, wherein for a substantially normally incident light and for at least one wavelength in a visible wavelength range from about 420 nm to about 680 nm, the plurality of microlayers transmits at least 60% of the incident excitation light for each of mutually orthogonal first and second polarization states.

3. The optical stack of claim 1, wherein:
   for the first incident angle, the microlayer optical transmittance of the plurality of microlayers versus wavelength comprises a first peak at a first peak wavelength with a corresponding full width at half maximum (FWHM) that comprises the excitation, but not the converted, wavelength; and
   for the second incident angle, the microlayer optical transmittance of the plurality of microlayers versus wavelength comprises a second peak at a second peak wavelength with a corresponding FWHM that comprises the converted, but not the excitation, wavelength.

4. An optical device for sensing a presence of an analyte, the optical device comprising:
   the optical stack of claim 3;
   a light source configured to emit the incident excitation light having the excitation wavelength and incident on the first optical filter at the first incident angle, the test sample converting at least the portion of the incident excitation light to the converted light at least after at least the portion of the incident excitation light is transmitted by the first optical filter, at least the portion of the converted light exiting the optical stack at least after the portion of the converted light is transmitted by the first optical filter at the second incident angle; and
an optical sensor configured to receive and sense the converted light exiting the optical stack.

5. An optical stack comprising a test sample disposed on a first optical filter, the test sample configured to convert at least a portion of an incident excitation light having an excitation wavelength to a converted light having at least one converted wavelength different from the excitation wavelength, the first optical filter comprising a plurality of microlayers numbering at least 20 in total, each of the plurality of microlayers having an average thickness of less than about 500 nanometers (nm), such that the plurality of microlayers has:
an optical transmittance T1>20% at the excitation wavelength and at a first incident angle;
an optical transmittance T2>20% at the at least one converted wavelength and at a second incident angle; and
an optical reflectance R1>40% at least one of the excitation wavelength and the at least one converted wavelength and at least one of the first incident angle and the second incident angle;
wherein:
for the at least one of the excitation and the at least one converted wavelength, a corresponding optical transmittance of the first optical filter changes by at least a factor of 2 when an initial incident angle corresponding to the at least one of the excitation and the at least one converted wavelength changes to the initial incident angle corresponding to the other one of the excitation and the at least one converted wavelength; and
for the second incident angle, a microlayer optical transmittance of the plurality of microlayers versus wavelength comprises at least a first peak with a corresponding first full width at half maxima (FWHM) that comprises the excitation, but not the converted, wavelength, and a second peak with a corresponding second FWHM that comprises the converted, but not the excitation, wavelength, wherein each of the corresponding first FWHM and the corresponding second FWHM is less than 200 nm wide.

6. The optical stack of claim 5, wherein for a substantially normally incident light and for at least one wavelength in a visible wavelength range from about 420 nm to about 680 nm, the plurality of microlayers transmits at least 60% of the incident excitation light for each of mutually orthogonal first and second polarization states.

7. An optical stack comprising a test sample disposed on a first optical filter, the test sample configured to convert at least a portion of an incident excitation light having an excitation wavelength to a converted light having at least one converted wavelength different from the excitation wavelength, the first optical filter comprising a plurality of microlayers numbering at least 20 in total, each of the plurality of microlayers having an average thickness of less than about 500 nanometers (nm), such that the plurality of microlayers has:
an optical transmittance T1>20% at the excitation wavelength and at a first incident angle;
an optical transmittance T2>20% at the at least one converted wavelength and at a second incident angle; and
an optical reflectance R1>40% at least one of the excitation wavelength and the at least one converted wavelength and at least one of the first incident angle and the second incident angle;
wherein:
for the at least one of the excitation and the at least one converted wavelength, a corresponding optical transmittance of the first optical filter changes by at least a factor of 2 when an initial incident angle corresponding to the at least one of the excitation and the at least one converted wavelength changes to the initial incident angle corresponding to the other one of the excitation and the at least one converted wavelength; and
for the second incident angle less than about 10 degrees, a microlayer optical transmittance of the plurality of microlayers versus wavelength comprises a band edge separating a higher transmission band comprising shorter wavelengths from a lower transmission band comprising longer wavelengths, the higher transmission band comprising the excitation and the at least one converted wavelength, such that increasing the second incident angle by less than about 60 degrees, shifts the higher transmission band and the lower transmission band so that the higher transmission band comprises the excitation wavelength and the lower transmission band comprises the at least one converted wavelength.

8. The optical stack of claim 7, wherein for a substantially normally incident light and for at least one wavelength in a visible wavelength range from about 420 nm to about 680 nm, the plurality of microlayers transmits at least 60% of the incident excitation light for each of mutually orthogonal first and second polarization states.

9. An optical device for sensing a presence of an analyte, the optical device comprising:
a sensor material emitting a second light having a second wavelength when irradiated with a first light having a different first wavelength, a first optical property of the emitted second light being sensitive to the presence of the analyte; and
an optical filter disposed on the sensor material and comprising a plurality of microlayers numbering at least 20 in total, each of the plurality of microlayers having an average thickness of less than about 500 nm, such that for at least a second incident angle, an optical transmission of the plurality of microlayers versus wavelength comprises a transmission band edge disposed between the different first wavelength and the second wavelength;
wherein, for the second incident angle, a microlayer optical transmittance of the plurality of microlayers versus wavelength comprises a lower transmission band separating a first higher transmission band and a second higher transmission band, the first higher transmission band comprising an excitation wavelength and the second higher transmission band comprising at least one converted wavelength.

10. The optical device of claim 9, wherein for a substantially normally incident light and for at least one wavelength in a visible wavelength range from about 420 nm to about 680 nm, the plurality of microlayers transmits at least 60% of the incident excitation light for each of mutually orthogonal first and second polarization states.

11. The optical device of claim 9, wherein:
for the first incident angle, the microlayer optical transmittance of the plurality of microlayers versus wavelength comprises a first peak at a first peak wavelength with a corresponding full width at half maximum (FWHM) that comprises the excitation, but not the converted, wavelength; and for the second incident angle, the microlayer optical transmittance of the plurality of microlayers versus wavelength comprises a second peak at a second peak wavelength with a corresponding FWHM that comprises the converted, but not the excitation, wavelength.

12. An optical device for sensing a presence of an analyte, the optical device comprising:

a sensor material emitting a second light having a second wavelength when irradiated with a first light having a different first wavelength, a first optical property of the emitted second light being sensitive to the presence of the analyte; and an optical filter disposed on the sensor material and comprising a plurality of microlayers numbering at least 10 in total, each of the plurality of microlayers having an average thickness of less than about 750 nm, wherein:

for a first incident angle, a microlayer optical transmittance of the plurality of microlayers versus wavelength comprises at least a first peak and a second peak with a first full width at half maxima (FWHM) and a second FWHM, the first FWHM comprising the different first wavelength, but not the second wavelength, the second FWHM comprising the second wavelength, but not the different first wavelength, each of the first FWHM and the second FWHM less than about 300 nm wide; and for a different second incident angle, the microlayer optical transmittance of the plurality of microlayers versus wavelength is less than about 10% at the different first wavelength and comprises at least a third peak with a corresponding third FWHM that comprises the second, but not the first, wavelength.

13. The optical device of claim 12, wherein the at least the first peak and the second peak further comprises a third fourth peak with a corresponding fourth FWHM that does not comprise either the second wavelength or the different first wavelength.

14. The optical device of claim 12, wherein for a substantially normally incident light and for at least one wavelength in a visible wavelength range from about 420 nm to about 680 nm, the plurality of microlayers transmits at least 60% of the incident excitation light for each of mutually orthogonal first and second polarization states.

* * * * *